(12) United States Patent
Py

(10) Patent No.: US 9,604,740 B2
(45) Date of Patent: Mar. 28, 2017

(54) CONTROLLED NON-CLASSIFIED FILLING DEVICE AND METHOD

(71) Applicant: Dr. Py Institute, LLC, New Milford, CT (US)

(72) Inventor: Daniel Py, Larchmont, NY (US)

(73) Assignee: DR. PY INSTITUTE LLC, New Milford, CT (US)

( * ) Notice: Subject to any disclaimer, the term of this patent is extended or adjusted under 35 U.S.C. 154(b) by 239 days.

(21) Appl. No.: 14/214,890

(22) Filed: Mar. 15, 2014

(65) Prior Publication Data

US 2014/0311617 A1 Oct. 23, 2014

Related U.S. Application Data

(60) Provisional application No. 61/798,210, filed on Mar. 15, 2013.

(51) Int. Cl.
| | |
|---|---|
| *B65B 31/00* | (2006.01) |
| *B65B 3/00* | (2006.01) |
| *A61M 5/00* | (2006.01) |
| *A61M 5/178* | (2006.01) |
| *A61J 1/14* | (2006.01) |
| *A61J 3/00* | (2006.01) |

(52) U.S. Cl.
CPC ............. *B65B 3/003* (2013.01); *A61J 1/1406* (2013.01); *A61J 1/1425* (2015.05); *A61J 3/002* (2013.01); *A61M 5/002* (2013.01); *A61M 5/1782* (2013.01); *A61J 2200/10* (2013.01)

(58) Field of Classification Search
CPC ...... B65B 3/003; A61J 1/1406; A61M 5/1782
USPC .......................................................... 141/329
See application file for complete search history.

(56) References Cited

U.S. PATENT DOCUMENTS

| | | | |
|---|---|---|---|
| 4,545,497 A | 10/1985 | Martha, Jr. | |
| 4,954,149 A | 9/1990 | Fullemann | |

(Continued)

FOREIGN PATENT DOCUMENTS

| | | |
|---|---|---|
| WO | WO2011/137413 A1 | 11/2011 |
| WO | WO 2012/177933 A1 | 12/2012 |

OTHER PUBLICATIONS

International Search Report and Written Opinion of the International Searching Authority for International Application No. PCT/US2014/030052.

*Primary Examiner* — Jason K Niesz
(74) *Attorney, Agent, or Firm* — McCarter & English, LLP

(57) ABSTRACT

An injection member penetrates an elastic septum of a device defining a sealed, empty, sterile chamber in fluid communication with the septum. During penetrating, an annular interface is formed between the septum and the injection member extending axially between a penetration point on an interior surface of the septum in fluid communication with the sterile chamber, and an exterior surface of the septum engaging the injection member. The injection member is de-contaminated by (i) friction between the septum and injection member at the annular interface, and (ii) elongation of the septum at the annular interface. A substance is introduced through the injection member and into the sterile chamber of the device, the injection member is then withdrawn from the septum, the septum reseals itself at the resulting penetration aperture, and the chamber is maintained sterile throughout the foregoing steps.

42 Claims, 24 Drawing Sheets

(56) References Cited

U.S. PATENT DOCUMENTS

| | | | |
|---|---|---|---|
| 5,656,035 A | 8/1997 | Avoy | |
| 6,478,775 B1 * | 11/2002 | Galt | A61B 17/00491 604/158 |
| 6,604,561 B2 | 8/2003 | Py | |
| 6,684,916 B2 | 2/2004 | Py | |
| 6,805,170 B2 | 10/2004 | Py | |
| 6,929,040 B2 | 8/2005 | Py | |
| 7,032,631 B2 | 4/2006 | Py | |
| 7,096,896 B2 | 8/2006 | Py | |
| 7,100,646 B2 | 9/2006 | Py | |
| 7,111,649 B2 | 9/2006 | Py | |
| 7,243,689 B2 | 7/2007 | Py | |
| 7,270,158 B2 | 9/2007 | Py | |
| 7,322,491 B2 | 1/2008 | Py | |
| 7,445,033 B2 | 11/2008 | Py | |
| 7,490,639 B2 | 2/2009 | Py | |
| 7,500,498 B2 | 3/2009 | Py | |
| 7,556,066 B2 | 7/2009 | Py | |
| 7,628,184 B2 | 12/2009 | Py | |
| 7,669,390 B2 | 3/2010 | Py | |
| 7,707,807 B2 | 5/2010 | Py | |
| 7,726,352 B2 | 6/2010 | Py | |
| 7,726,357 B2 | 6/2010 | Py et al. | |
| 7,780,023 B2 | 8/2010 | Py | |
| 7,810,529 B2 | 10/2010 | Py | |
| 7,905,257 B2 | 3/2011 | Py | |
| 7,954,521 B2 | 6/2011 | Py | |
| 7,967,034 B2 | 6/2011 | Py | |
| 7,975,453 B2 | 7/2011 | Py | |
| 7,980,276 B2 | 7/2011 | Py | |
| 7,992,597 B2 | 8/2011 | Py | |
| 8,096,333 B2 | 1/2012 | Py | |
| 8,112,972 B2 | 2/2012 | Py | |
| 8,347,923 B2 | 1/2013 | Py | |
| 8,376,003 B2 | 2/2013 | Py | |
| 8,408,256 B2 | 4/2013 | Py | |
| 8,631,838 B2 | 1/2014 | Py | |
| 8,646,243 B2 | 2/2014 | Py | |
| 8,671,964 B2 | 3/2014 | Py | |
| 8,739,838 B2 | 6/2014 | Py | |
| 2006/0231519 A1 * | 10/2006 | Py | B65D 51/002 215/342 |
| 2007/0225635 A1 * | 9/2007 | Lynn | A61M 39/045 604/30 |
| 2009/0098250 A1 | 4/2009 | Py | |
| 2009/0139953 A1 | 6/2009 | Py | |
| 2010/0051575 A1 | 3/2010 | Ou et al. | |
| 2010/0236659 A1 | 9/2010 | Py | |
| 2011/0277873 A1 | 11/2011 | Py | |
| 2012/0152881 A1 | 6/2012 | Py | |
| 2012/0261027 A1 | 10/2012 | Py | |
| 2013/0008137 A1 | 1/2013 | Py | |
| 2013/0190704 A1 | 7/2013 | Py | |
| 2013/0270820 A1 | 10/2013 | Py | |
| 2013/0292592 A1 | 11/2013 | Py | |
| 2015/0122369 A1 * | 5/2015 | Py | A61M 39/26 141/1 |

* cited by examiner

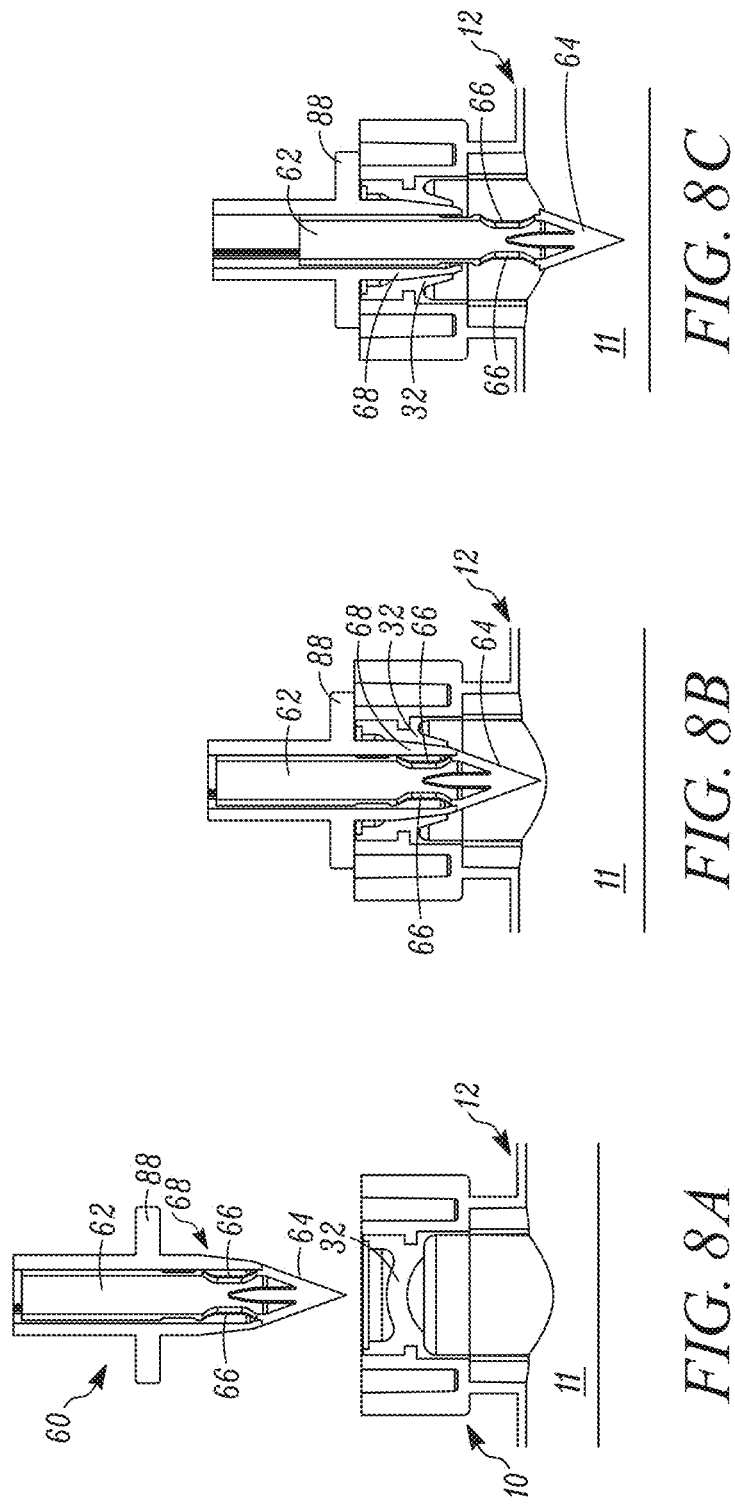

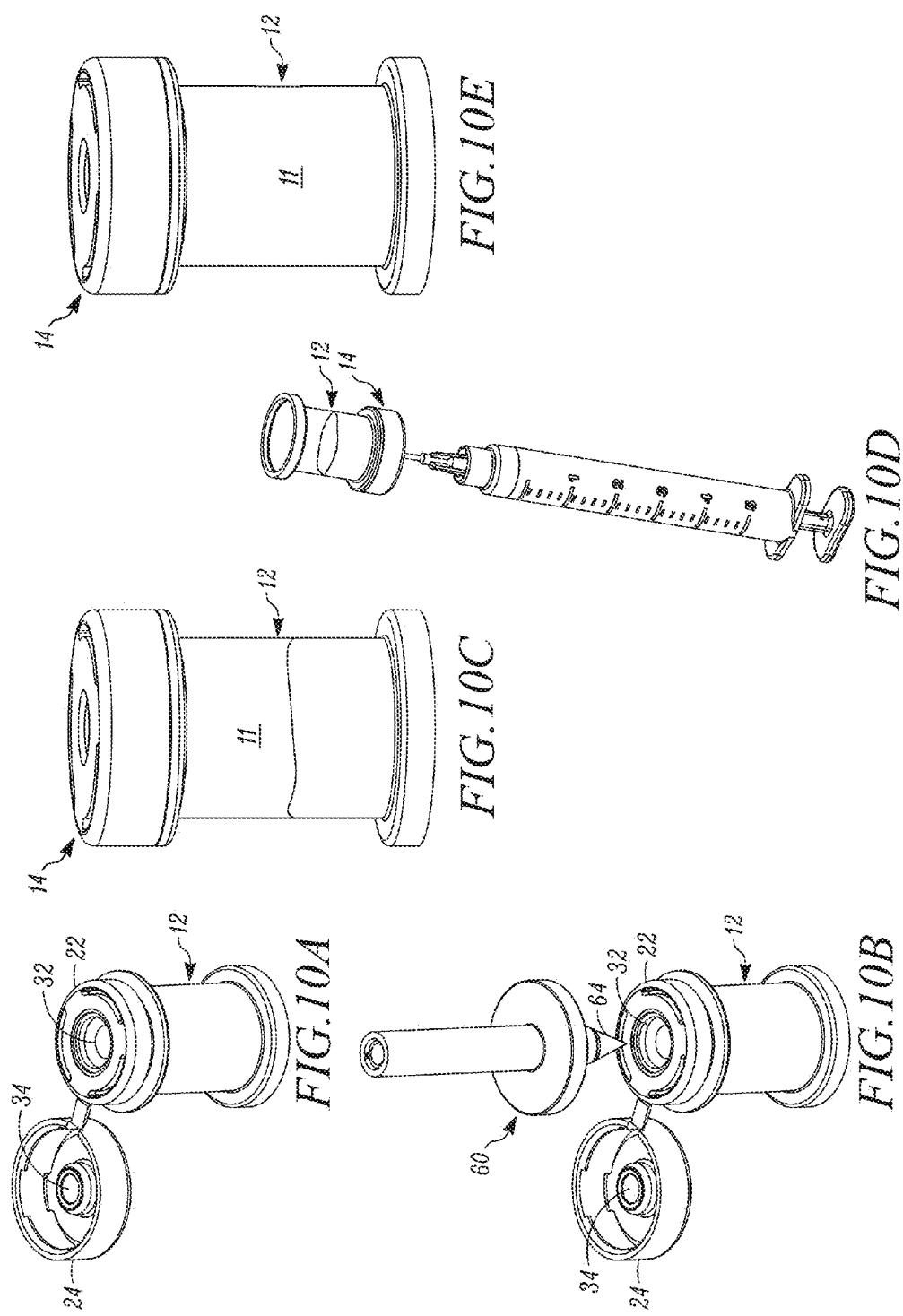

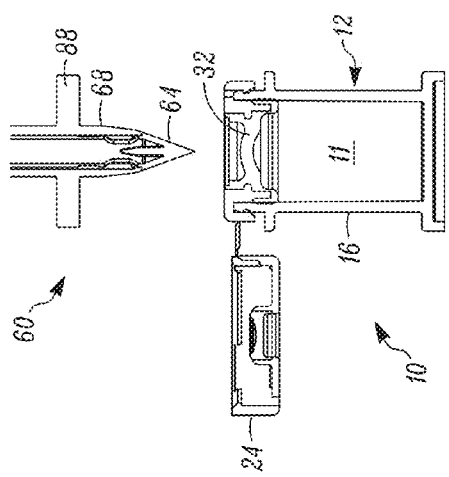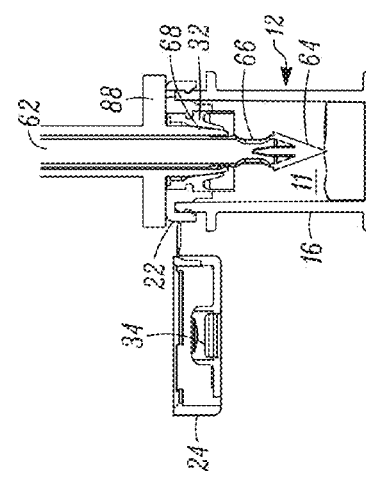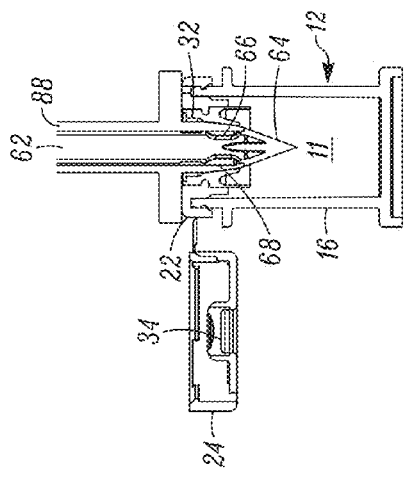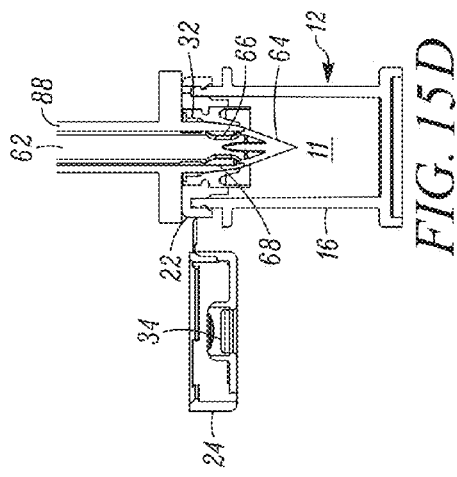

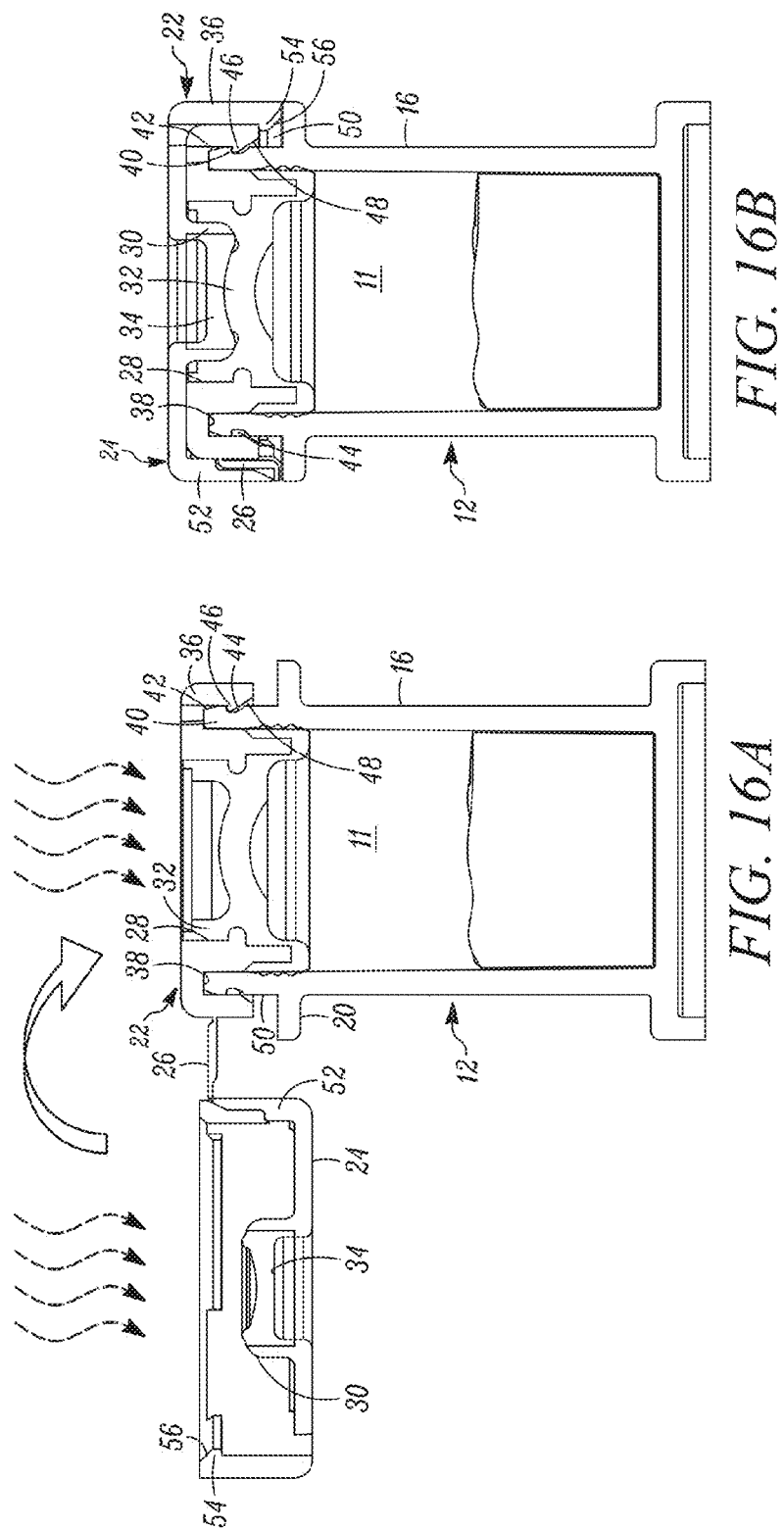

CONTROLLED NON-CLASSIFIED FILLING DEVICE AND METHOD

CROSS-REFERENCE TO RELATED APPLICATIONS

This patent application claims benefit under 35 U.S.C. §119 to similarly-titled U.S. Provisional Patent Application No. 61/798,210, filed Mar. 15, 2013, which is hereby incorporated by reference in its entirety as part of the present disclosure.

FIELD OF THE INVENTION

The present invention relates to devices and methods for sterile or aseptic filling of substances, such as liquids, gels, creams, gases or powders, into devices or containers, and more specifically, to such devices and methods that sterile or aseptic fill closed containers and devices.

BACKGROUND OF THE INVENTION

A cleanroom is an environment, typically used in manufacturing or scientific research, that has a low level of environmental pollutants such as dust, airborne microbes, aerosol particles and chemical vapors. A cleanroom has a controlled level of contamination that is specified by the number of particles per cubic meter at a specified particle size. To give perspective, the ambient air outside in a typical urban environment contains 35,000,000 particles per cubic meter in the size range 0.5 µm and larger in diameter, corresponding to an ISO 9 cleanroom, while an ISO 1 cleanroom allows no particles in that size range and only 12 particles per cubic meter of 0.3 µm and smaller.

Cleanrooms can be very large. Entire manufacturing facilities can be contained within a cleanroom with factory floors covering thousands of square meters. They are used extensively in semiconductor manufacturing, biotechnology, the life sciences and other fields that are very sensitive to environmental contamination.

The air entering a cleanroom from outside is filtered to exclude dust, and the air inside is constantly recirculated through high-efficiency particulate air (HEPA) and/or ultra-low penetration air (ULPA) filters to remove internally generated contaminants. Staff enter and leave through airlocks (sometimes including an air shower stage), and wear protective clothing such as hoods, face masks, gloves, boots and coveralls. Equipment inside the cleanroom is designed to generate minimal air contamination. Only special mops and buckets are used. Cleanroom furniture is designed to produce a minimum of particles and to be easy to clean. Common materials such as paper, pencils, and fabrics made from natural fibers are often excluded, and alternatives used. Some cleanrooms are kept at a positive pressure so that if there are any leaks, air leaks out of the chamber instead of unfiltered air coming in. Some cleanroom HVAC systems control the humidity to low levels, such that extra equipment is necessary (e.g., "ionizers") to prevent electrostatic discharge (ESD) problems.

Cleanrooms maintain particulate-free air through the use of either HEPA or ULPA filters employing laminar or turbulent airflow principles. Laminar, or unidirectional, air flow systems direct filtered air downward in a constant stream towards filters located on walls near the cleanroom floor or through raised perforated floor panels to be recirculated. Laminar airflow systems are typically employed across about 80 percent of a cleanroom ceiling to maintain constant air processing. Stainless steel or other non-shed materials are used to construct laminar airflow filters and hoods to prevent excess particles entering the air. Turbulent, or non-unidirectional, airflow uses both laminar airflow hoods and non-specific velocity filters to keep air in a cleanroom in constant motion, although not all in the same direction. The rough air seeks to trap particles that may be in the air and drive them towards the floor, where they enter filters and leave the cleanroom environment.

In the pharmaceutical industry, the term "isolator" covers a variety of pieces of equipment. One group has the main objective of providing containment for the handling of dangerous materials either aseptically or not. Another group has the main objective of providing a microbiologically controlled environment within which aseptic operations can be carried out. Containment isolators often employ negative internal air pressure and most isolators used for aseptic processing employ positive pressure. A sporicidal process, usually delivered by gassing, can be used to aid microbiological control. Some large-scale isolators provide an opening, often called a mouse hole, to permit continuous removal of sealed product. Other isolators remain sealed throughout production operations.

Aseptic operations can include sterility testing or aseptic processing to produce medicinal products. Isolators are used to provide a microbiologically controlled environment for aseptic processing for producing medicinal products labeled as sterile. Isolators could be seen as a more encompassing development of the barriers used in conventional clean rooms. The clean room barriers evolved from plastic flexible curtains through to rigid barriers with glove ports. The objectives of barriers are to increasingly separate the surrounding clean room including the operator from the critical zone where aseptic operations are carried out and sterile materials are exposed. When the degree of containment is nearly complete, sporicidal procedures can be applied without harming the operators. Accordingly, an isolator is an arrangement of physical barriers that are integrated to the extent that the isolator can be sealed in order to carry out a routine leak test based on pressure to meet specified limits. Internally it provides a workspace, which is separated from the surrounding environment. Manipulations can be carried out within the space from the outside without compromising its integrity. Industrial isolators used for aseptic processing are isolators in which the internal space and exposed surfaces are microbiologically controlled. Control is achieved by the use of microbiologically retentive filters, sterilization processes, sporicidal processes (such as by gassing) and prevention of recontamination from the external environment. A sporicidal process is a gaseous, vapor or liquid treatment applied to surfaces, using an agent that is recognized as capable of killing bacterial and fungal spores. The process is applied to internal surfaces of the isolator and external surfaces of materials inside the isolator, when conventional sterilization methods are not required.

Cleanrooms are classified according to the number and size of particles permitted per volume of air. Large numbers like "class 100" or "class 1000" refer to FED-STD-209E, and denote the number of particles of size 0.5 µm or larger permitted per cubic foot of air. The standard also allows interpolation, so it is possible to describe, for example, "class 2000". Small numbers refer to ISO 14644-1 standards, which specify the decimal logarithm of the number of particles 0.1 µm or larger permitted per cubic meter of air. For example, an ISO class 5 cleanroom has at most $10^5=100,000$ particles per cubic meter. Because 1 $m^3$ is approximately 35 $ft^3$, the two standards are mostly equivalent when measuring 0.5 µm particles, although the testing standards differ. Ordinary room air is approximately class 1,000,000 or ISO 9. A discrete-particle-counting, light-scattering instrument is used to determine the concentration of airborne particles, equal to and larger than the specified sizes, at designated sampling locations.

| US FED STD 209E Cleanroom Standards | | | | | | |
|---|---|---|---|---|---|---|
| | maximum particles/ft³ | | | | | ISO |
| Class | ≥0.1 μm | ≥0.2 μm | ≥0.3 μm | ≥0.5 μm | ≥5 μm | equivalent |
| 1 | 35 | 7.5 | 3 | 1 | 0.007 | ISO 3 |
| 10 | 350 | 75 | 30 | 10 | 0.07 | ISO 4 |
| 100 | 3,500 | 750 | 300 | 100 | 0.7 | ISO 5 |
| 1,000 | 35,000 | 7,500 | 3000 | 1,000 | 7 | ISO 6 |
| 10,000 | 350,000 | 75,000 | 30,000 | 10,000 | 70 | ISO 7 |
| 100,000 | $3.5 \times 10^6$ | 750,000 | 300,000 | 100,000 | 700 | ISO 8 |

| ISO 14644-1 Cleanroom Standards | | | | | | | |
|---|---|---|---|---|---|---|---|
| | maximum particles/m³ | | | | | | FED STD 209E |
| Class | ≥0.1 μm | ≥0.2 μm | ≥0.3 μm | ≥0.5 μm | ≥1 μm | ≥5 μm | equivalent |
| ISO 1 | 10 | 2.37 | 1.02 | 0.35 | 0.083 | 0.0029 | |
| ISO 2 | 100 | 23.7 | 10.2 | 3.5 | 0.83 | 0.029 | |
| ISO 3 | 1,000 | 237 | 102 | 35 | 8.3 | 0.29 | Class 1 |
| ISO 4 | 10,000 | 2,370 | 1,020 | 352 | 83 | 2.9 | Class 10 |
| ISO 5 | 100,000 | 23,700 | 10,200 | 3,520 | 832 | 29 | Class 100 |
| ISO 6 | $1.0 \times 10^6$ | 237,000 | 102,000 | 35,200 | 8,320 | 293 | Class 1,000 |
| ISO 7 | $1.0 \times 10^7$ | $2.37 \times 10^6$ | 1,020,000 | 352,000 | 83,200 | 2,930 | Class 10,000 |
| ISO 8 | $1.0 \times 10^8$ | $2.37 \times 10^7$ | $1.02 \times 10^7$ | 3,520,000 | 832,000 | 29,300 | Class 100,000 |
| ISO 9 | $1.0 \times 10^9$ | $2.37 \times 10^8$ | $1.02 \times 10^8$ | 35,200,000 | 8,320,000 | 293,000 | Room air |

Both FS 209E and ISO 14644-1 assume log-log relationships between particle size and particle concentration. For that reason, zero particle concentration does not exist. The table locations without entries are non-applicable combinations of particle sizes and cleanliness classes, and should not be read as zero.

| BS 5295 Cleanroom Standards | | | | | |
|---|---|---|---|---|---|
| | maximum particles/m³ | | | | |
| Class | ≥0.5 μm | ≥1 μm | ≥5 μm | ≥10 μm | ≥25 μm |
| Class 1 | 3,000 | | 0 | 0 | 0 |
| Class 2 | 300,000 | | 2,000 | 30 | |
| Class 3 | | 1,000,000 | 20,000 | 4,000 | 300 |
| Class 4 | | | 200,000 | 40,000 | 4,000 |

BS 5295 Class 1 also requires that the greatest particle present in any sample does not exceed 5 μm.

| GMP EU Classification | | | | |
|---|---|---|---|---|
| | maximum particles/m³ | | | |
| Class | At Rest 0.5 μm | At Rest 5 μm | In Operation 0.5 μm | In Operation 5 μm |
| Class A | 3,520 | 20 | 3,500 | 20 |
| Class B | 3,520 | 29 | 352,000 | 2,900 |
| Class C | 352,000 | 2,900 | 3,520,000 | 29,000 |
| Class D | 3,520,000 | 29,000 | n/a | n/a |

The term "sterility assurance level" (SAL) is used in microbiology to describe the probability of a single unit being non-sterile after it has been subjected to a sterilization process. For example, medical device manufacturers design their sterilization processes for an extremely low SAL—"one in a million" devices should be nonsterile. SAL is also used to describe the killing efficacy of a sterilization process, where a very effective sterilization process has a very low SAL.

In microbiology, it is considered impossible to prove that all organisms have been destroyed because: 1) they could be present but undetectable simply because they are not being incubated in their preferred environment, and 2) they could be present but undetectable because their existence has never been discovered. Therefore, SALs are used to describe the probability that a given sterilization process has not destroyed all of the microorganisms.

Mathematically, SALs referring to probability are usually very small numbers and so are properly expressed as negative exponents (e.g., "The SAL of this process is 10 to the minus six"). SALs referring to sterilization efficacy are usually much larger numbers and so are properly expressed as positive exponents (e.g., "The SAL of this process is 10 to the six"). In this usage, the negative effect of the process is sometimes inferred by using the word "reduction" (e.g., "This process gives a six-log reduction").

SALs can be used to describe the microbial population that was destroyed by a sterilization process. Each log reduction ($10^{-1}$) represents a 90% reduction in microbial population. So a process shown to achieve a "6-log reduction" ($10^{-6}$) will reduce a population from a million organisms ($10^6$) to very close to zero.

In order to sterile or aseptically fill substances into containers or devices, such as pharmaceuticals, vaccines, and food products, cleanrooms and isolators have been employed in order to ensure the requisite SALs to maintain the filled product aseptic or sterile. However, as summarized above, cleanrooms and isolators can require substantial capital expenditures, operational costs, numerous controls, sophisticated and expensive facilities, and/or highly trained personnel. Accordingly, it would be desirable to sterile or aseptically fill substances without such cleanrooms and/or isolators, while nevertheless ensuring the requisite SALs to maintain the filled substances aseptic or sterile.

It is therefore an object of the present invention to overcome one or more of the above-described drawbacks and/or disadvantages of the prior art.

SUMMARY OF THE INVENTION

In accordance with one aspect, a method comprises the following steps:
(a) penetrating an elastic septum of a device with an injection member, wherein the device defines a sealed, empty, sterile chamber in fluid communication with the elastic septum;
(b) during the penetrating step, forming an annular interface between the elastic septum and the injection member extending axially between a penetration point on an interior surface of the elastic septum in fluid communication with the sterile chamber, and an exterior surface of the septum engaging the injection member, and de-contaminating the injection member by at least one of (i) friction between the elastic septum and injection member at the annular interface, and (ii) elongation of the elastic septum at the annular interface;
(c) introducing a substance through the injection member and into the sterile chamber of the device;
(d) withdrawing the injection member from the elastic septum;
(e) allowing the elastic septum to reseal itself at a penetration aperture resulting from withdrawal of the injection member; and
(f) maintaining the chamber sterile throughout steps (a) through (e).

Some embodiments comprise performing the penetrating step in an ambient environment defining a level of contamination greater than about class 100 or ISO 5. Some such embodiments comprise performing steps a) through e) in an ambient environment defining a level of contamination greater than about class 100 or ISO 5. Some embodiments comprise performing the penetrating step in an ambient environment defining a level of contamination greater than about class 100 or ISO 5 and less than or equal to about class 100,000 or ISO 8.

In some embodiments, the de-contaminating of the injection member includes achieving at least approximately a 3 log reduction in bio-burden at the annular interface between the elastic septum and injection member. In some such embodiments, the de-contaminating of the injection member includes achieving at least approximately a 5 log reduction in bio-burden at the annular interface between the elastic septum and injection member. In some such embodiments, the de-contaminating of the injection member includes achieving at least approximately a 6 log reduction in bio-burden at the annular interface between the elastic septum and injection member.

Some embodiments further comprise resealing the resulting penetration aperture. In some such embodiments, the resealing step includes resealing the resulting penetration aperture with a mechanical seal, a liquid sealant, a thermal seal, and/or a chemical seal. Some embodiments further comprise transmitting radiation onto the resulting penetration aperture to effect or further effectuate the seal.

In some embodiments, the elastic septum includes a penetration zone defining an approximate dome-shape, and the penetrating step includes penetrating the elastic septum in the dome-shape penetration zone. In some such embodiments, the elastic septum defines a substantially convex exterior surface, and a substantially concave interior surface opposite the convex exterior surface. In some such embodiments, the interior surface of the septum defines a relatively recessed surface extending substantially about the penetration zone. In some such embodiments, the relatively recessed surface is a groove.

In some embodiments, the elastic septum defines a penetration zone that is penetrated by the injection member, and the penetration zone is shaped to enhance the pressure exerted by the elastic septum onto the injection member during the penetrating step. In some such embodiments, the penetration zone of the elastic septum is approximately dome shaped. In some such embodiments, the approximately dome-shaped penetration zone defines a substantially convex exterior surface, and a substantially concave interior surface.

In some embodiments, during the penetrating step, the internal surface of the elastic septum forms an initial crack at substantially the maximum elongation of the elastic septum by the injection member.

In some embodiments, the annular interface is defined by a portion of the penetrated elastic septum extending annularly about the injection member substantially throughout an axial distance extending between the interior and exterior points of contact between the penetrated septum and injection member. In some embodiments, the axial distance is at least about ½ mm. In some embodiments, the axial distance is at least about 1 mm. And in some such embodiments, the axial distance is at least about 1⅓ mm.

In some embodiments, the annular interface between the elastic septum and injection member defines a substantially inverted, frusto-conical shape.

In some embodiments, the coefficient of friction of the septum-engaging surface of the injection member is less than the coefficient of friction of the penetrated portion of the elastic septum.

Some embodiments further comprise reducing strain on an interior surface of the septum within a zone of penetration of the injection member during the penetrating step with a groove formed on an interior surface of the septum and extending substantially about the zone of penetration. In some such embodiments, the groove extends annularly about and adjacent or contiguous to the zone of penetration.

In some embodiments, the injection member includes at least one port for dispensing the substance from the injection member, and the method further includes sealing the port with respect to the ambient atmosphere until at least a portion of the port is in fluid communication with the sterile chamber. Some such embodiments further comprise moving at least one of a closure and the port of the injection member from a closed position sealing the port with respect to ambient atmosphere to an open position opening the port into fluid communication with the sterile chamber. Some such embodiments further comprise, before or during the withdrawing step, moving at least one of the closure and the port of the injection member from the open position to the closed position. Some such embodiments further comprise introducing the substance from the injection member into the sterile chamber after perforating the elastic septum, or after part of the port passes through an interior surface of the elastic septum and is in fluid communication with the sterile chamber. Some such embodiments further comprise substantially sealing the port and an interior of the injection member from ambient atmosphere in the closed position. In some embodiments, the sealing includes forming a substantially fluid-tight seal with a relatively soft material at the interface of the closure and injection member. Some embodiments further comprise during the penetrating and withdrawing steps, substantially preventing contact between the port and the elastic septum. Some such embodiments further comprise interposing the closure between the port and the elastic septum and substantially preventing contact between the port and the elastic septum.

In some embodiments, the elastic septum is self-closing and substantially prevents the ingress of fluid through the resulting penetration aperture. Some embodiments further comprise introducing a toxic substance through the injection member and into the sterile chamber of the device, and using the closure to prevent any exposure of the toxic substance to the ambient atmosphere throughout the method.

In some embodiments, the de-contaminating of the injection member includes exerting pressure with the elastic septum onto the injection member at the annular interface between the elastic septum and injection member and, in turn, killing organisms at the interface. In some such embodiments, the exerting pressure on the injection member includes penetrating a substantially dome or convex shaped portion of the elastic septum.

In some embodiments, the elastic septum defines a penetration zone that is penetrated by the injection member, and the penetration zone of the elastic septum defines a thickness prior to penetration within the range of about ½ to about two times an outer diameter of the injection member. In some embodiments, the elastic septum defines a penetration zone including a recess defining a reduced thickness of the elastic septum, and the penetrating step includes penetrating the elastic septum at the reduced thickness of the penetration zone. In some such embodiments, the penetration zone recess defines a substantially frusto-conical shape. In some embodiments, the injection member includes a penetrating tip defining a first included angle, and the penetration zone recess defines a second included angle that is substantially the same as the first included angle. In other embodiments, the injection member includes a penetrating tip defining a first included angle, and the penetration zone recess defines a second included angle that is greater than the first included angle.

In accordance with another aspect, a device that is sterile filled by an injection member defining a port that is normally sealed with respect to ambient atmosphere and can be opened to dispense substance from the injection member therethrough. The device comprises a body defining a sealed, empty, sterile chamber; and an elastic septum in fluid communication with sealed, empty, sterile chamber. The elastic septum is penetrable by the injection member and forms an annular interface between the elastic septum and the injection member extending axially between (i) a penetration point on an interior surface of the elastic septum in fluid communication with the sterile chamber, and (ii) an exterior surface of the septum engaging the injection member. Relative movement of at least one of the injection member and elastic septum relative to the other de-contaminates the injection member through (i) friction between the elastic septum and injection member at the annular interface, and/or (ii) elongation of the elastic septum at the annular interface.

In some embodiments, the relative movement of the injection member and elastic septum opens the port of the injection member into fluid communication with the sterile chamber to dispense substance from the injection member into the sterile chamber. In some embodiments, the relative movement opens the port after decontaminating the injection member at the annular interface and at least part of the port is passed through the septum.

In some embodiments, the relative movement of the injection member and elastic septum de-contaminates the injection member by at least approximately a 3 log reduction in bio-burden at the annular interface between the elastic septum and injection member. In some such embodiments, the relative movement of the injection member and elastic septum de-contaminates the injection member by at least approximately a 5 log reduction in bio-burden at the annular interface between the elastic septum and injection member. In some such embodiments, the relative movement of the injection member and elastic septum de-contaminates the injection member by at least approximately a 6 log reduction in bio-burden at the annular interface between the elastic septum and injection member.

The elastic member is in some embodiments re-sealable or capable of being resealed at the resulting penetration aperture. In some such embodiments, the resulting penetration aperture of the elastic member is re-sealed with at least one of a mechanical seal, a liquid sealant, a thermal seal, and/or a chemical seal.

In some embodiments, the elastic septum includes a penetration zone penetrable by the injection member and defining an approximate dome-shape. In some such embodiments, the elastic septum defines a substantially convex exterior surface, and a substantially concave interior surface opposite the convex exterior surface. In some such embodiments, the interior surface of the septum defines a relatively recessed surface extending substantially about the penetration zone. In some such embodiments, the relatively recessed surface is a groove. Some embodiments further comprise means for reducing the strain on an interior surface of the septum during penetration thereof by the injection member. In some such embodiments, the means is a groove formed on the interior surface of the septum and extending substantially about a zone of penetration of the septum by the injection member.

In some embodiments, the elastic septum defines a hardness within the range of about 1 to about 100 shore A. In some such embodiments, the elastic septum defines a hardness within the range of about 20 to about 80 shore A.

In some embodiments, the elastic septum defines a penetration zone that is penetrable by the injection member, and the penetration zone is shaped to enhance the pressure exerted by the elastic septum onto the injection member during penetration thereof by the injection member. In some such embodiments, the penetration zone of the elastic septum is approximately dome shaped. In some embodiments, the approximately dome-shaped penetration zone defines a substantially convex exterior surface, and a substantially concave interior surface.

In some embodiments, the annular interface is defined by a portion of the penetrated elastic septum extending annularly about the injection member substantially throughout an axial distance extending between the interior and exterior points of contact between the penetrated septum and injection member. In some such embodiments, the axial distance is at least about ½ mm. In some such embodiments, the axial distance is at least about 1 mm. And in some such embodiments, the axial distance is at least about 1⅓ mm.

In some embodiments, the annular interface between the elastic septum and injection member defines a substantially inverted, frusto-conical shape. In certain embodiments, the coefficient of friction of the penetrated portion of the elastic septum is greater than the coefficient of friction of the septum-engaging surface of the injection member.

Some embodiments further comprise means for reducing strain on an interior surface of the septum during penetration thereof by the injection member. In some such embodiments, the means is an annular groove formed on the interior surface of the septum and extending substantially about a zone of penetration of the injection member on the septum. In some such embodiments, the groove extends annularly about and adjacent or contiguous to the zone of penetration.

The elastic septum is in some embodiments self-closing and substantially prevents the ingress of fluid through the resulting penetration aperture. In some embodiments, the elastic septum is configured to exert pressure onto the injection member at the annular interface between the elastic septum and injection member to thereby kill organisms at the interface. In some such embodiments, the elastic septum includes a substantially dome or convex shaped zone of penetration that exerts pressure on the injection member during penetration thereof by the injection member.

In some embodiments, the elastic septum defines a penetration zone that is penetrated by the injection member, and the penetration zone of the elastic septum defines a thickness prior to penetration within the range of about ½ to about two times an outer diameter of the injection member.

In some embodiments, the elastic septum defines a penetration zone including a recess defining a reduced thickness of the elastic septum that is penetrated by the injection member. In some such embodiments, the penetration zone recess defines a substantially frusto-conical shape. In some embodiments, the injection member includes a penetrating tip defining a first included angle, and the penetration zone recess defines a second included angle that is substantially the same as the first included angle. In other embodiments, the injection member includes a penetrating tip defining a first included angle, and the penetration zone recess defines a second included angle that is greater than the first included angle.

In some embodiments, an apparatus for filling and resealing a container or other device is provided. The apparatus includes a housing at least partially defining a processing space and a device support for releasably holding a sealed device defining a sealed chamber for storing a substance therein, and a penetrable portion in fluid communication with the chamber and penetrable by a filling or injection member. The apparatus also includes a conveyor defining a path for transporting the support and the device along the path and through the processing space. Within the processing space of the apparatus, the apparatus includes a de-contamination station located on the conveyor path and configured to de-contaminate at least the penetrable surface of the penetrable septum, a filling station located on the conveyor path downstream of the de-contamination station and including at least one filling or injection member coupled or connectible in fluid communication with a source of substance to be filled into the chamber of the device. The filling or injection member and/or the device is movable relative to the other within the filling station to penetrate the penetrable septum with the filling or injection member, introduce substance through the filling or injection member and into the chamber, and withdraw the filling or injection member from the septum. A resealing station is located on the conveyor path downstream of the filling station and is configured to reseal an aperture formed in the septum during the filling of the chamber of the device at the filling station. In some embodiments, a cap storage station is configured for storing a cap removed from the filling or injection member during filling and resealing of the device.

In some embodiments, the apparatus for filling and resealing includes a cap removal device configured to remove the cap from the filling or injection member prior to filling of the device and store the cap in the cap storage station. The cap removal device is configured to retrieve the cap from the storage station after filling and resealing of the device, and reapply the cap to the filling or injection member, and then remove the capped filling or injection member from the apparatus In some embodiments, an apparatus for filling and resealing a container includes a housing at least partially defining a processing space, a device support for releasably holding a sealed device defining a sealed chamber for storing a substance therein, and a penetrable portion in fluid communication with the chamber and penetrable by a filling or injection member, and a conveyor defining a path for transporting the support and the device along the path and through the processing space. Within the processing space is a de-contamination station located on the conveyor path and configured to de-contaminate at least the penetrable surface of the penetrable septum, and a filling station located on the conveyor path downstream of the de-contamination station and including at least one filling or injection member coupled or connectible in fluid communication with a source of substance to be filled into the chamber of the device. The filling or injection member and/or the device is movable relative to the other within the filling station to penetrate the penetrable septum with the filling or injection member, introduce substance through the filling or injection member and into the chamber, and withdraw the filling or injection member from the septum. A resealing station is located on the conveyor path downstream of the filling station configured to reseal an aperture formed in the septum during the filling of the chamber of the device at the filling station. A source of substance is placeable into and removable from fluid communication with the filling station by a sterile connector that is configured to provide a fluid flow path between the source of substance and the filling station that is sealed from the ambient atmosphere when the source of substance is placed into fluid communication with the filling station and maintains the fluid flow path sealed from the ambient atmosphere when the source of substance is not in fluid communication with the filling station.

In some embodiments, the source of substance comprises a carousel or like support device configured to releasable retain one or more substance supply containers. Further, each of the one or more substance supply containers contains a different substance to be sterile filled, such as a respective ingredient, formula or composition, including substances in liquid, semi-liquid, gel and/or powder form. In other embodiments, the apparatus includes a control disposed between the source of substance and the filling station configured to control the flow of substance to be filled between the source of substance and the filling station. In some embodiments the flow path is sterile.

In other embodiments, a method is provided for filling and resealing a sealed container or other device. The method includes conveying a filling or injection member into a filling device, wherein the filling or injection member is housed within a cap. The filling device includes a housing at least partially defining a processing space, a device support for releasably holding a sealed device defining a sealed chamber for storing a substance therein, and a penetrable portion in fluid communication with the chamber and penetrable by a filling or injection member, a conveyor defining a path for transporting the support and the device along the path and through the processing space. Within the processing space, a de-contamination station is located on the conveyor path and configured to de-contaminate at least the penetrable surface of the penetrable septum, and a filling station is located on the conveyor path downstream of the de-contamination station and includes at least one filling or injection member coupled or connectible in fluid communication with a source of substance to be filled into the chamber of the device. The filling or injection member and/or the device is movable relative to the other within the filling station to penetrate the penetrable septum with the filling or injection member, introduce substance through the filling or injection member and into the chamber, and withdraw the filling or injection member from the septum. A resealing station is located on the conveyor path downstream of the filling station and is configured to reseal an aperture formed in the septum during the filling of the chamber of the device at the filling station. The method further includes removing the filling or injection member from the cap and fluidly connecting the filling or injection member to a source of substance, storing the cap of the filling or injection member in the filling device at a storage position, de-contaminating at least a penetrable surface of a device including a needle penetrable portion or septum penetrable by a filling or injection member and a sealed chamber in fluid communication with the penetrable septum, moving the filling or injection member and/or the device relative to the other to penetrate the penetrable septum with the filling or injection member, introducing substance through the filling or injection member and into the chamber, and withdrawing the filling or injection member from the septum, and sealing the penetrated region of the septum.

In other embodiments, the method includes the steps of retrieving the cap from the storage position and re-attaching the cap to the filling or injection member.

One advantage of certain embodiments is that the annular interface decontaminates the injection member by at least one, and in some embodiments both, of (i) friction between the elastic septum and injection member at the annular interface, and (ii) elongation of the elastic septum at the annular interface, and therefore there is no need to sterilize or otherwise decontaminate the injection member prior filling, or to sterilize or otherwise decontaminate the ambient environment in which the filling occurs. Yet another advantage of certain embodiments is that the injection member is sealed with respect to the ambient atmosphere until it penetrates the elastic septum and the de-contaminated portion of the injection member is in fluid communication with the sterile chamber of the device. This further obviates the need to fill within a de-contaminated or controlled environment. Accordingly, the filling can be performed in an ambient environment defining a level of contamination greater than about class 100 or ISO 5, such as an ambient environment defining a level of contamination greater than about class 100 or ISO 5 and less than or equal to about class 100,000 or ISO 8. Such a controlled, non-classified ambient environment can obviate the substantial capital expenditures, operational costs, numerous controls, sophisticated and expensive facilities, and/or highly trained personnel, required by the prior art as described above.

Yet another advantage is that the de-contaminating of the injection member can achieve at least approximately a 3 log reduction in bio-burden at the annular interface between the elastic septum and injection member, in some embodiments at least approximately a 5 log reduction in bio-burden at the annular interface between the elastic septum and injection member, and in further embodiments at least approximately a 6 log reduction in bio-burden at the annular interface between the elastic septum and injection member. Accordingly, the features of some embodiments can ensure significant levels of sterility assurance without many of the drawbacks and disadvantages of the prior art.

Other objects and advantages of the present invention, and/or of embodiments thereof, will become more readily apparent in view of the following detailed description and accompanying drawings.

BRIEF DESCRIPTION OF THE DRAWINGS

FIG. 8A is a partial, side cross-sectional view of the closure and tip of the filling device of FIG. 6 prior to engagement with the septum of the vial of FIG. 1, with the closure in the first or closed position sealing the ports from ambient atmosphere;

FIG. 8B is a side cross-sectional view of the filling device of FIG. 6 upon penetration of the tip of the filling or injection member through the septum of the type shown in FIG. 1, with the closure still in the first or closed position sealing the ports from contact with the penetrated septum;

FIG. 8C is a side cross-sectional view of the filling device of FIG. 6 wherein the tip of the filling member is penetrated through the septum, the closure is prevented from further movement through the septum, and the filling member is allowed to continue to move into the chamber relative to the fixed closure to expose the fluid ports to the chamber and allow the aseptic or sterile flow of substance through the open ports and into the aseptic or sterile chamber;

FIG. 10A is a top perspective view of a device in the form of a vial, with the second closure in the first, non-sealing position;

FIG. 10B is a top perspective view the device of FIG. 10A with the second closure in the first, non-sealing position with a filling member positioned to pierce the first closure;

FIG. 10C is a side view of the device of FIG. 10A that has been filled, with the second closure in the second, sealing position;

FIG. 10D is a side view of the filled device of FIG. 10C with a needle piercing the second closure into the chamber to permit withdrawal of substance from the chamber;

FIG. 10E is a side view of the device of FIG. 10C with all of the substance withdrawn from the chamber;

FIG. 15A is a cross-sectional view of the device and filling member shown in FIG. 10B;

FIG. 15B is a cross-sectional view of the device of FIG. 10A with the tip of the filling member penetrating the septum of the first closure into the chamber and the closure of the filling member in the first or closed position, sealing the ports of the filling member from the ambient atmosphere;

FIG. 15C is a cross-sectional view of the device of FIG. 10A with the filling member further penetrating into the chamber with the closure of the filling member in the second or open position, opening the ports of the filling member;

FIG. 15D is a cross-sectional view of the device of FIG. 10A with the filling member partially withdrawn from the chamber and the closure of the filling member moved back to the first or closed position, re-sealing the ports of the filling member from the ambient atmosphere;

FIG. 16A is a cross-sectional view of the device of FIG. 10A after the filling member has pierced the vial septum and been withdrawn leaving a hole in the vial septum, with the second closure in the first, non-sealing position, and schematically showing sterilization of the first and second closures;

FIG. 16B is a cross-section view of the device of FIG. 16A with the second closure in the second, sealing position, enclosing the hole in the vial septum;

DETAILED DESCRIPTION OF EMBODIMENTS OF THE INVENTION

Figure 1:
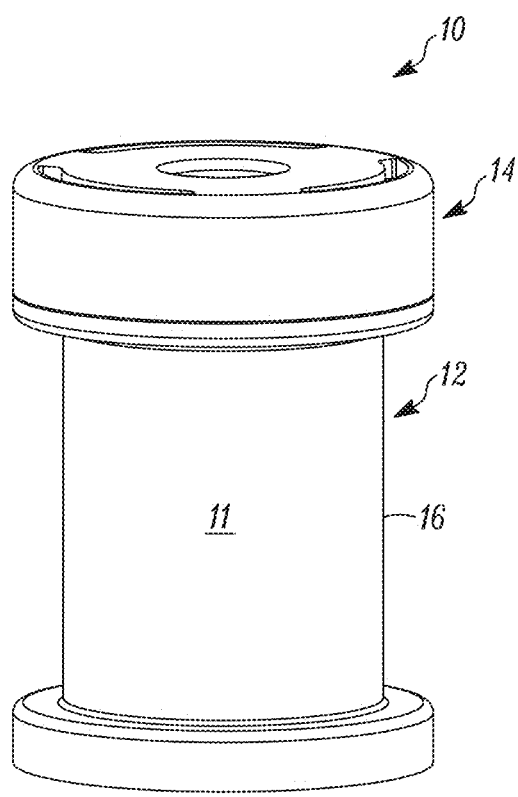
FIG. 1 is a side perspective view of a device in the form of a vial.
Figure 2:
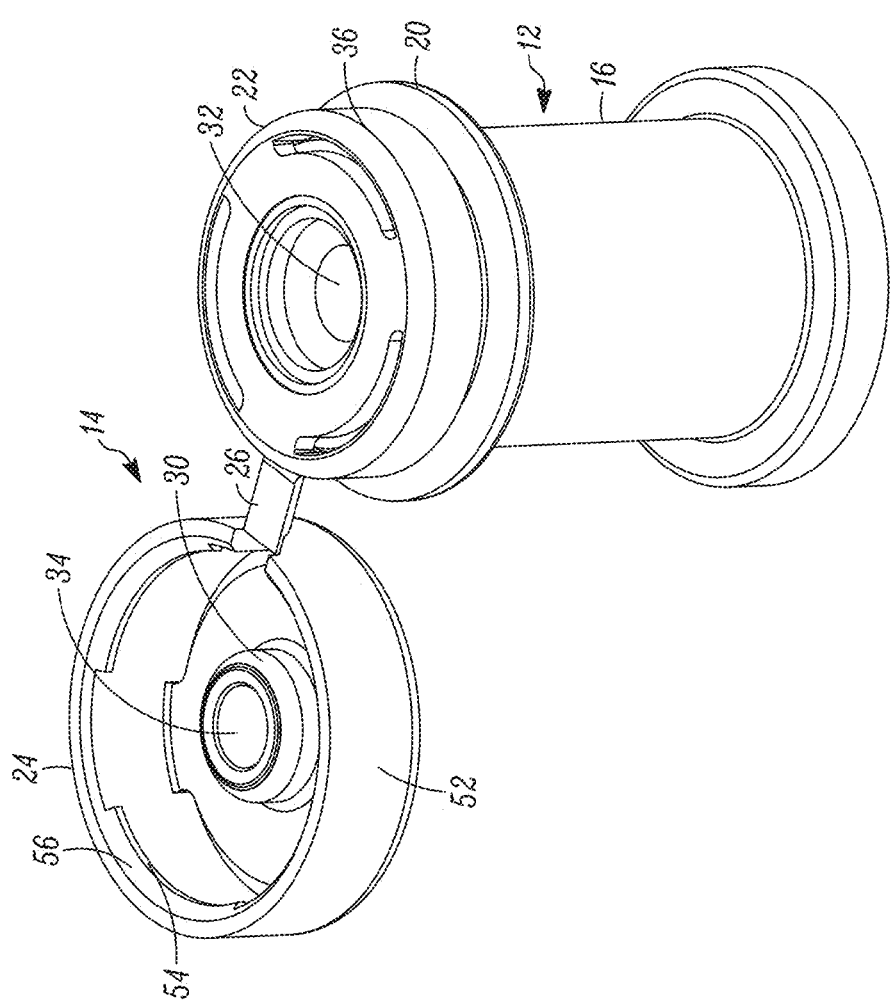
FIG. 2 is a top perspective view of the vial of FIG. 1, with a second closure in the first, non-sealing position.

In FIG. 1, a device is indicated generally by the reference numeral 10. In the illustrated embodiment, the device 10 is a vial defining a sealed empty chamber 11 therein for aseptic or sterile filling with a substance, such as a medicament, pharmaceutical injectable, or vaccine. However, as may be recognized by those of ordinary skill in the pertinent art based on the teachings herein, the invention may be embodied in and otherwise may be applicable to any of numerous different types of devices that are currently known or that later become known, such as containers, syringes, delivery devices, dispensers and processing devices. Similarly, the devices may be filled with any of numerous different substances that are currently known or that later become known, such as medicaments, pharmaceutical injectables, vaccines, supplements, foods, beverages, liquid nutrition products, and industrial products, and in any of numerous different forms, including liquids, gels, powders and gases.

As shown in FIG. 1, the vial 10 includes a vial body 12 and a closure 14. In the illustrated embodiment, the body is substantially cylindrical and defines a substantially cylindrical sidewall 16 with an annular aperture 18 at a top end thereof, for sealingly receiving the closure 14 thereon, as described further below. The vial body 12 further includes an annular projection 20 spaced from the top end thereof and extending laterally outward from the sidewall 16. The vial body 12 may be made of glass or plastic. However, as may be recognized by those of ordinary skill in the pertinent art based on the teaching herein, the body may be made of any of numerous different materials that are currently known or that later become known. As also may be recognized by those of ordinary skill in the pertinent art based on the teachings herein, the body may be configured in any of numerous shapes to receive a closure. For example, the body may define a spool-like or "diabolo" shape such as disclosed in U.S. Pat. No. 7,100,646, issued Sep. 5, 2006, entitled "Sealed Containers and Methods of Making and Filling Same," which, in turn, claims priority from similarly titled U.S. Provisional Patent Application No. 60/408,068, filed Sep. 3, 2002, each of which is hereby expressly incorporated by reference in its entirety as part of the present disclosure.

As shown in FIG. 2, FIG. 10A, FIG. 11D and FIG. 13, the closure 14 comprises a first closure 22 and a second closure 24. The first and second closures 22, 24 are moveable with respect to one another. In the illustrated embodiment, the first and second closures are coupled via a living hinge 26. However, as may be recognized by those of ordinary skill in the pertinent art based on the teachings herein, the second closure may be connected to either of the first closure or vial body via any of numerous connections that are currently known or that later become known to allow movement of at least one of the closures relative to the other. Similarly, the first and second closures 22, 24 need not be connected in the open position, but rather may be connected only in the closed position when the second closure overlies and sealingly engages a penetration aperture in the first closure. Where the first and second closures 22, 24 are connected in the open position, they may be molded in one piece, as shown.

Figure 11D:
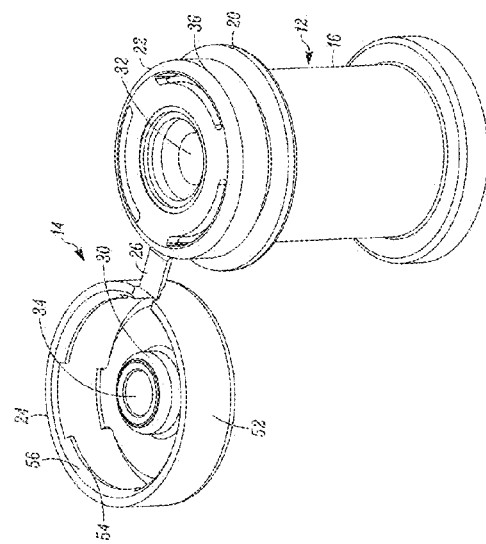
FIGS. 11A-11D sequentially show the assembly of the device of FIG. 10A, in which the septa are over-molded onto the molded cap and the first closure is sealingly closed in place on the vial.
Figure 11C:
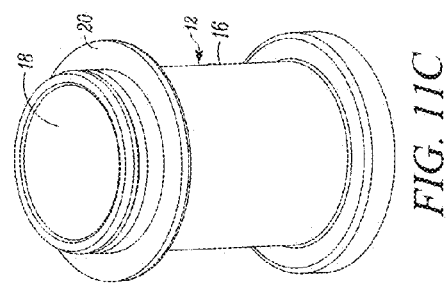
Figure 11B:
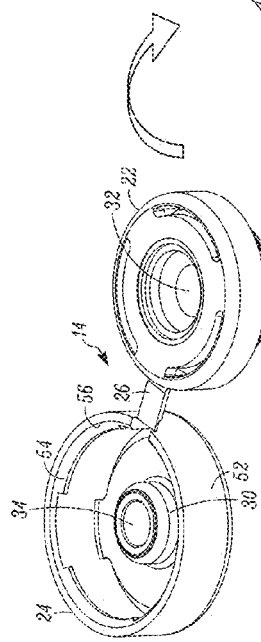
Figure 11A:
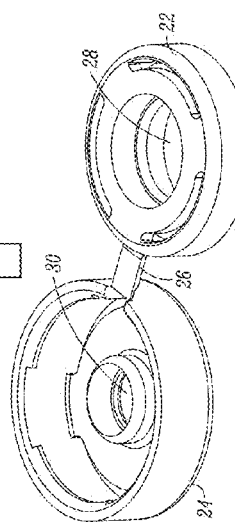
Figure 14:
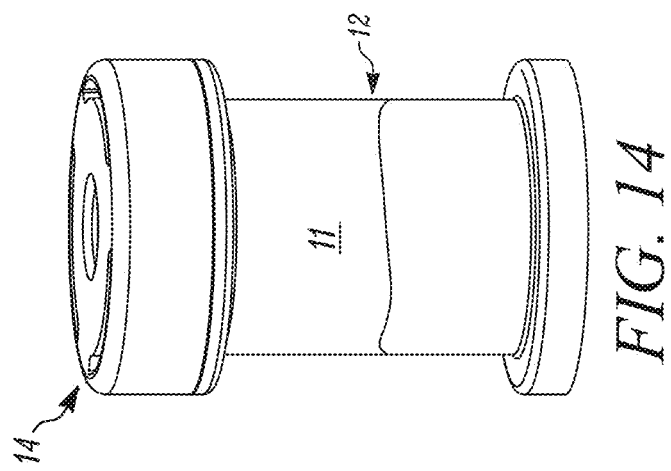
FIG. 14 is a side view of the device of FIG. 13 that has been filled, with the second closure in the second, sealing position, and the hole in the first closure formed by a filing member sealingly enclosed by the second closure.
Figure 13:
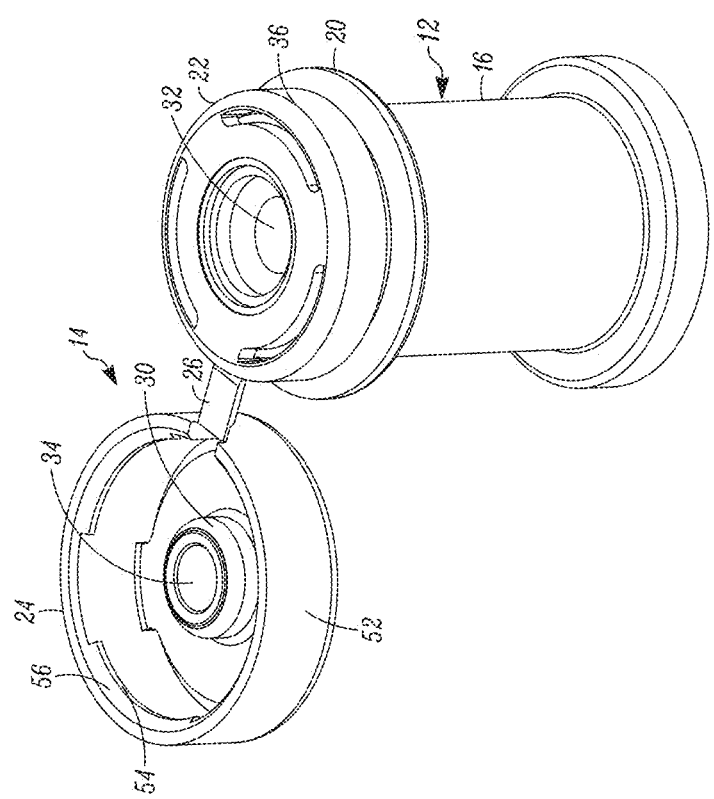
FIG. 13 is a top perspective view of the device of FIG. 10A with the second closure in the first, non-sealing position, and the device is ready for filing.

Both the first and second closures 22, 24 include first and second substantially centered recesses 28, 30 respectively, axially extending from the top surfaces of the closures for sealingly receiving therein first and second penetrable septums 32, 34, respectively. The penetrable septums may be made of any needle-penetrable elastomeric, rubber or rubber-like material that is sufficiently elastic to be penetrated by a needle. In some embodiments, the septum materials also are sufficiently elastic to close a resulting penetration aperture after removal of a needle or like injection member therefrom to thereby reseal itself. In some embodiments, the first and second penetrable septums 32, 34 are co-molded with the first and second closure portions 22, 24, respectively. In other embodiments, the first and second penetrable septums 32, 34 are over-molded with the first and second closure portions 22, 24, respectively, e.g., at the same time, as shown in FIGS. 11A and 11B. The second closure portion 24 can then be mounted onto the vial body 12 as shown in FIGS. 11C and 11D. However, as may be recognized by those of ordinary skill in the pertinent art based on the teachings herein, the penetrable septums may be configured in any of numerous different ways that are currently known or that later become known, to seal the first septum with the second septum. Alternatively, the device may not include a second septum, but rather the resulting penetration aperture in the first septum may be resealed in another manner, as described further below.

Figure 3:
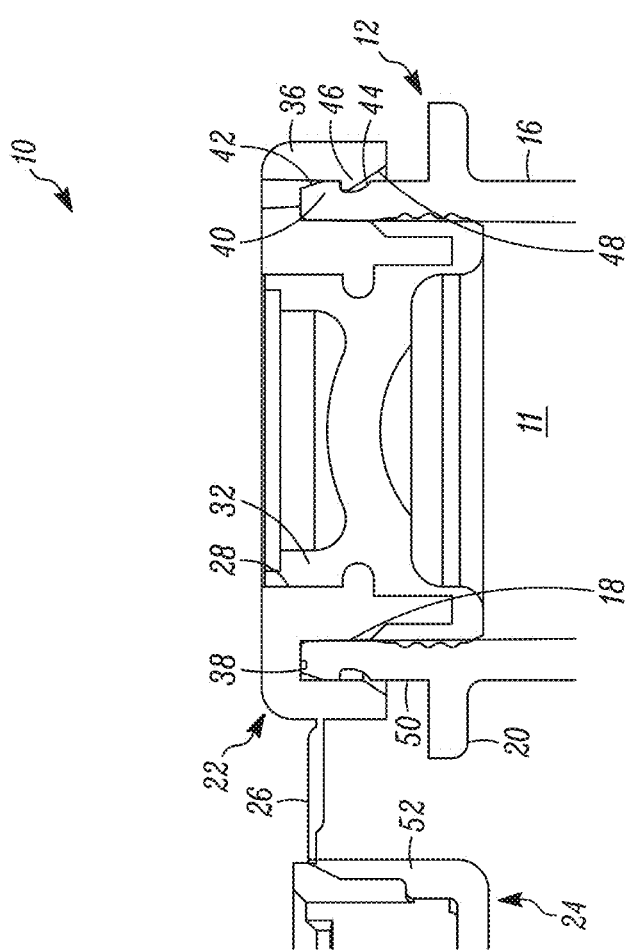
FIG. 3 is a partial, side cross-sectional side view of the vial of FIG. 1, with the second closure in the first, non-sealing position.
Figure 12:
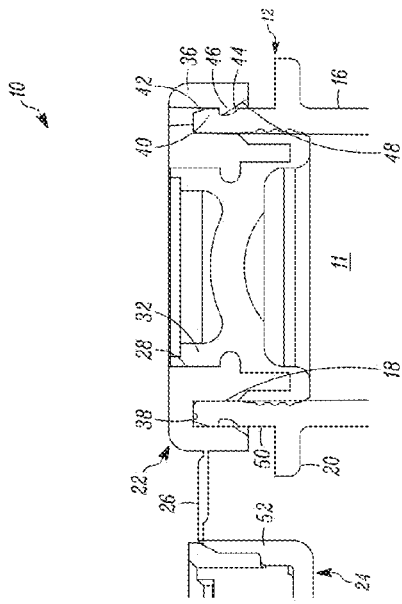
FIG. 12 is a partial, side cross-sectional side view of the device of FIG. 10A, with the first closure in the closed position.

As shown in FIG. 3 and FIG. 12, the first closure 22 includes an annular sidewall 36 axially extending from the perimeter of the top surface thereof, defining an axially extending annular channel 38 between the annular sidewall 36 and the annular wall of the annular recess 28. The annular channel 38 receives therein a portion of the top end of the cylindrical sidewall 16 of the body 12, when the first closure is mounted atop the body. The top end of the cylindrical sidewall 16 of the body defines an annular tapered protuberance 40. As can be seen, the tapered protuberance 40 defines a tapered surface 42 on an external side of the sidewall 16. Directly adjacent to the body tapered protuberance 40, opposite the top end of the body, the body sidewall 16 defines a laterally extending annular recess 44, extending inwardly from the exterior of the sidewall.

The bottom end of the annular sidewall 36 of the first closure defines a corresponding annular tapered protuberance 46. As can be seen, the tapered protuberance 46 defines a tapered surface 48 on the interior of the sidewall 36. Thus, when the first closure 22 is mounted atop the body 12, a portion of the sidewall at the top end of the body is received within the axially-extending annular channel 38 of the first closure, and the annular tapered protuberance 46 of the first closure slides past the opposing annular tapered protuberance 40 of the body and snaps into the laterally-extending annular recess 44 of the body to create a fluid-tight seal therebetween. Another annular recess 50 is defined between the bottom end of the first closure and the laterally-extending annular projection 20 of the body.

When the first closure 22 is sealingly mounted atop the body 12, the sealed empty chamber 11 is defined within the body, and the first penetrable septum 32 is in fluid communication with the chamber. If the sealed, empty device, and/or the closure 14 and body 12, are sterilized, a sealed, empty, sterile chamber is thus defined therein. Sterilization of the device, or of the closure, body and/or any component parts therein, may be achieved in any of numerous different ways that are currently known, or that later become known, such as by applying radiation thereto (e.g., gamma, ebeam, UV or other type of sterilizing radiation), or by application of a fluid sterilant (e.g, vaporized hydrogen peroxide or nitric oxide), and/or the sealed empty chamber may be sterilized prior to filling with a fluid sterilant as disclosed in U.S. Provisional Patent Application Ser. No. 61/499,626, filed Jun. 21, 2011, entitled "Nitric Oxide Injection Sterilization Device and Method," which is hereby expressly incorporated by reference in its entirety as part of the present disclosure as if fully set forth herein.

With the first closure 22 mounted atop the body 12, the second closure 24 is moveable between a first position (shown in FIG. 2, FIG. 10A, FIG. 11D and FIG. 13), spaced away from the first closure 22, and a second position (shown in FIG. 4), where the second closure 24 mounts atop the first closure 22. In the first position, the second penetrable septum 34 is not sealingly engaging the first penetrable septum 32. In the second position, on the other hand, the second penetrable septum 34 sealingly overlies the penetrable portion of the first penetrable septum 32, thus creating a mechanical seal, as explained further below. Alternatively, as also explained below, the second septum may be eliminated, and the resulting penetration aperture in the first septum may be resealed in any of numerous different ways that are currently known, or that later become known, such as by laser or other form of radiation, by applying thermal energy, and/or by applying a liquid sealant, such as liquid silicone.

Figure 5:
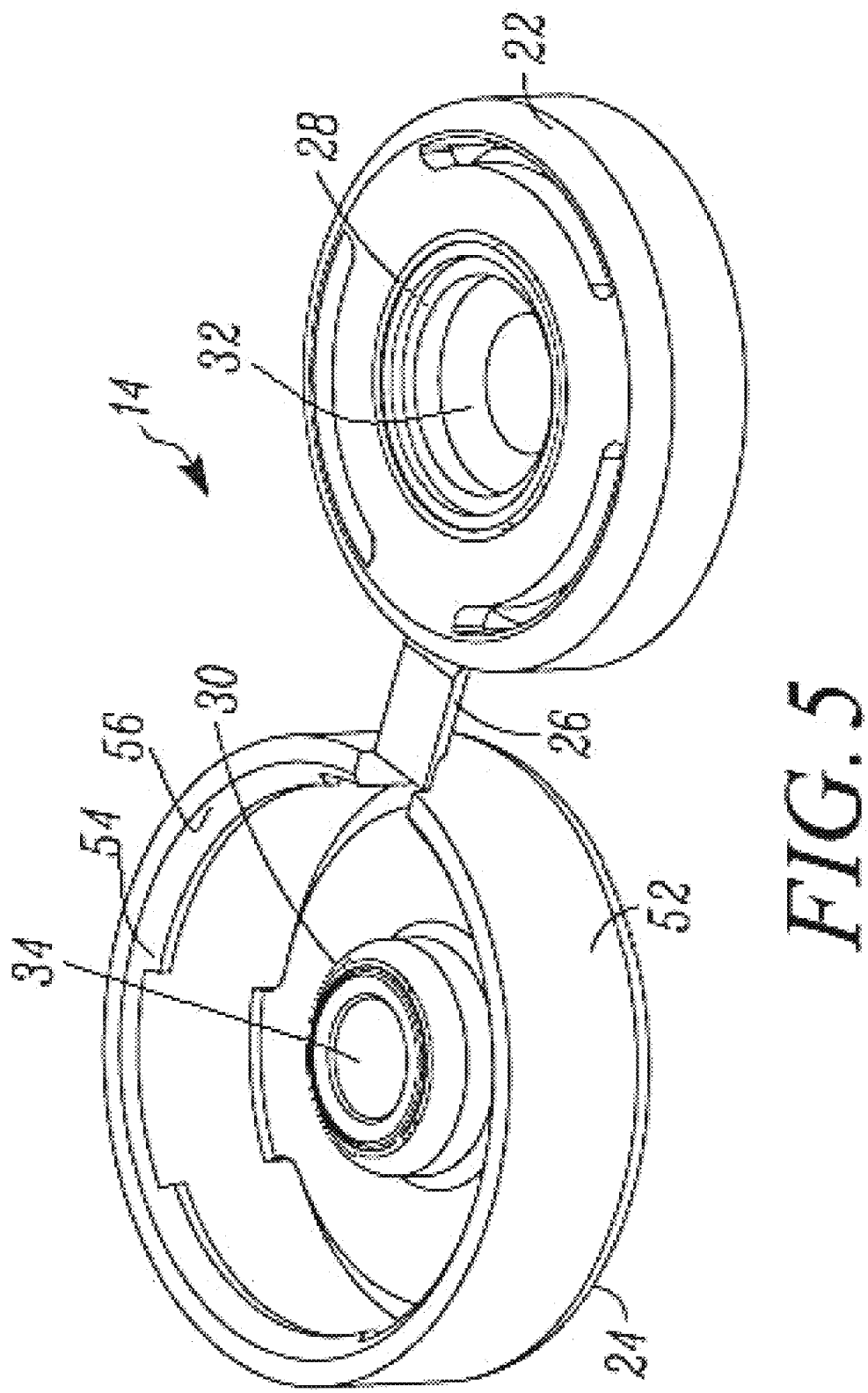
FIG. 5 is an upper perspective view of the first and second closures of the vial of FIG. 1, with the second closure in the first, non-sealing position.

As shown in FIG. 5 and FIG. 11B, the second closure 24 includes an annular sidewall 52 axially extending from the perimeter of the top surface thereof, and is configured to fittingly receive the first closure 24 therein when in the second position. The bottom end of the second closure annular sidewall 52 defines an annular tapered protuberance 54. As can be seen, the tapered protuberance 54 defines a tapered surface 56 on the internal side of the sidewall 52. When the second closure 24 is moved from the first position to the second position, the first closure is fittingly received within the second closure, the bottom end of the second closure abuts the laterally-extending annular projection 20 of the body, and the annular tapered protuberance 54 of the second closure snaps into the annular recess 50 between the bottom end of the first closure and the laterally-extending annular projection to secure the second closure in the second position.

Figure 4:
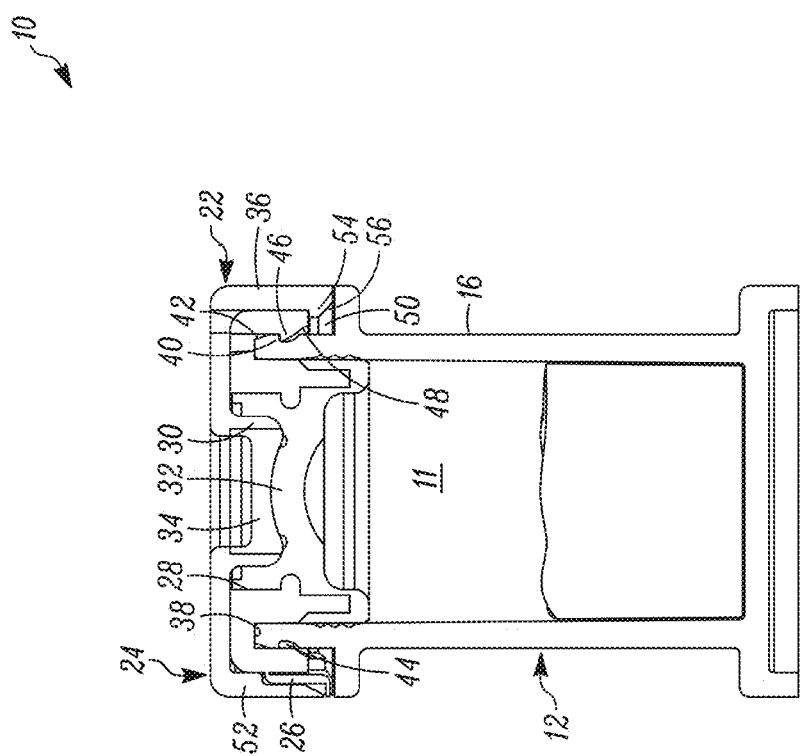
FIG. 4 is a side cross-sectional view of the vial of FIG. 1, with the second closure in the second, sealing position.

When in the second position, the second axially-extending recess 30 of the second closure 24, containing the second penetrable septum 34 therein, sealingly fits within the first penetrable septum 32, thereby sealingly engaging the second penetrable septum atop the penetrable portion of the first penetrable septum. In the illustrated embodiment, as shown in FIG. 4, the first penetrable septum 32 is approximately dome or convex shaped on a side thereof opposite the chamber 11. The second penetrable septum 34 is correspondingly approximately dome or convex shaped as well on a side thereof substantially opposite the first penetrable septum 32, in order to sealingly mate with the contour of the first penetrable septum.

In order to fill the device 10 with a substance, a filling device penetrates the first penetrable septum 32, when the second closure 24 is in the second or open position. An exemplary needle is disclosed in U.S. patent application Ser. No. 13/450,306, filed Apr. 18, 2012, entitled "Needle with Closure and Method," which, in turn, claims priority to U.S. Provisional Patent Application Ser. No. 61/476,523, filed Apr. 18, 2011, entitled "Filling Needle and Method," each of which is hereby expressly incorporated by reference in its entirety as part of the present disclosure as if fully set forth herein.

Figure 6:
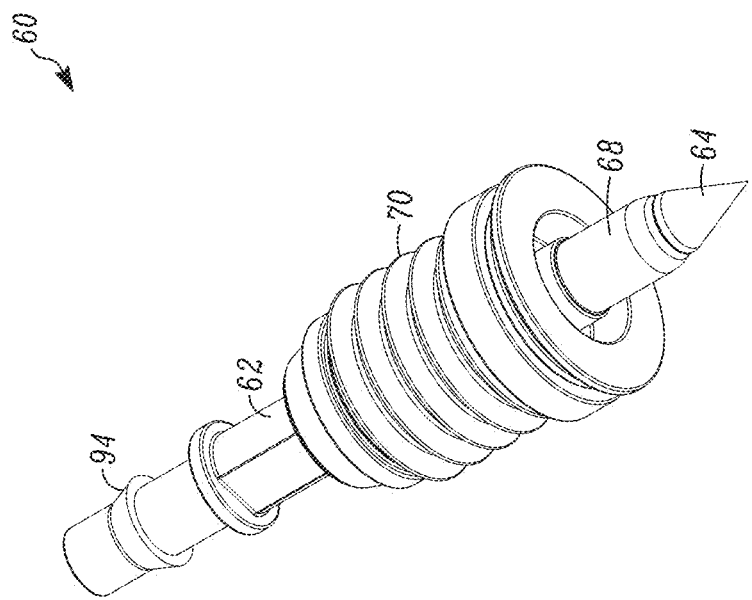
FIG. 6 is a side perspective view of a filling device engageable with the vial of FIG. 1 to aseptically or sterile fill a substance therein.

In some embodiments, a filling device 60, as shown in FIG. 6, is utilized to fill the device 10. The filling device 60 comprises a hollow filling or injection member 62, a tip 64 formed at one end of the filling member, two ports 66 in fluid communication with the interior of the hollow filling member 62, a first or relatively rigid closure 68, and a second closure or relatively flexible annular shell 70. The filling member 62 includes a boss 72 (FIG. 7B) at approximately a middle portion thereof. As can be seen, the boss 72 defines an annularly and axially extending recess therein for receiving a proximal portion of the closure 68 and a biasing member 74 that engages and biases the closure, as described further below. In the illustrated embodiments, the two ports 66 are diametrically opposed relative to each other; however, as may be recognized by those of ordinary skill in the pertinent art based on the teachings herein, the filling device may define any number of ports that may define any of numerous different configurations and locations.

Figures 7A, 7B:
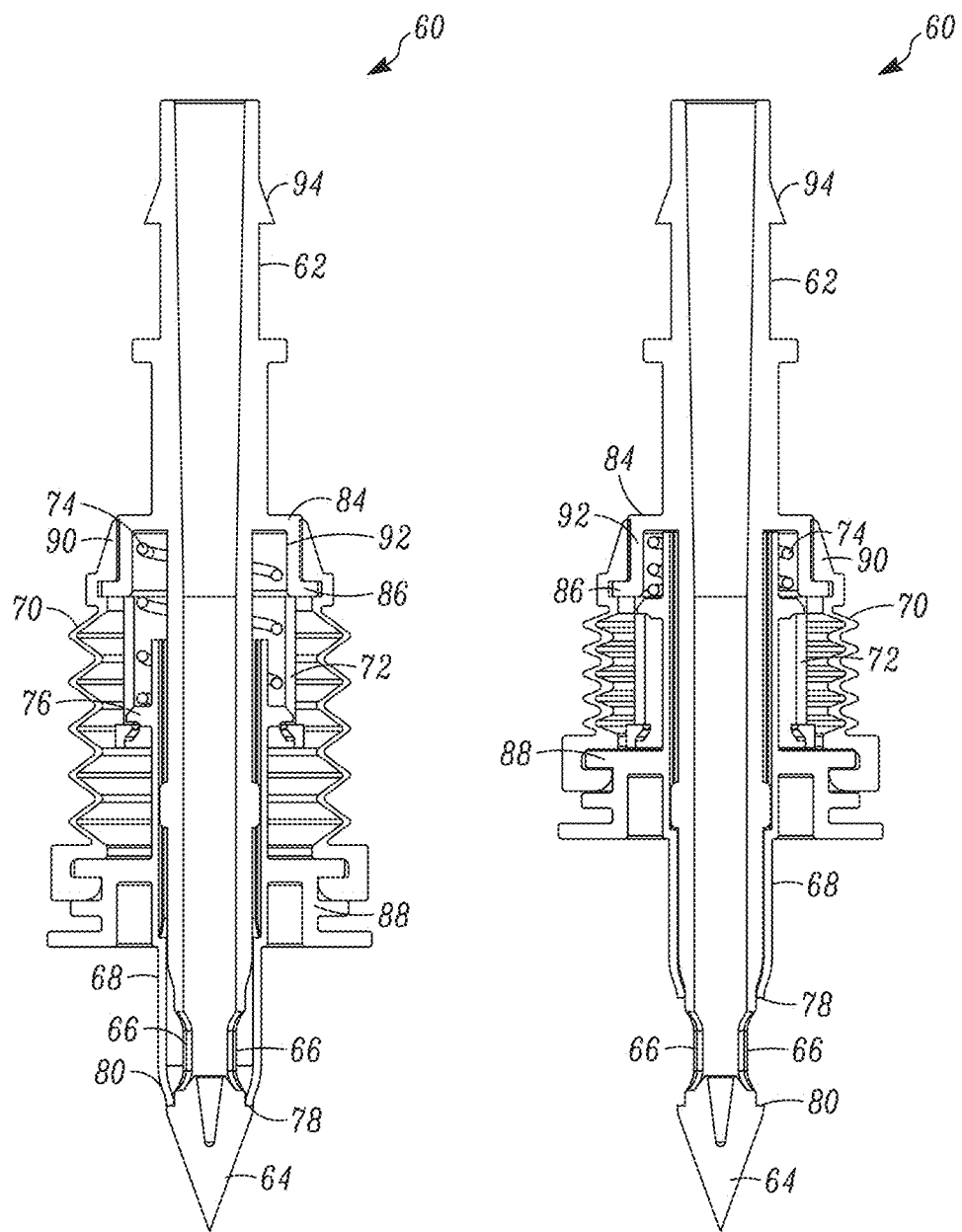
FIG. 7A is a side cross-sectional view of the filling device of FIG. 6, with the closure in the first or closed position, sealing the ports of the filling member from the ambient atmosphere.
FIG. 7B is a side cross-sectional view of the filling device of FIG. 6, with the closure in the second or open position, opening the ports of the filling member.

The closure 68 and/or the filling member 62 is movable between (i) a first position wherein the closure closes the ports 66, as shown typically in FIG. 7A, and (ii) a second position opening the ports 66, as shown typically in FIG. 7B. When in the closed position, the closure 68 forms a substantially fluid-tight seal between the ports 66 and ambient atmosphere. The closure 68 is biased via the biasing member 74 in the direction from the second or open position toward the first or closed position to normally close the ports 66. In the illustrated embodiment, the biasing member 74 is a coil spring. However, as may be recognized by those of ordinary skill in the pertinent art based on the teachings herein, the closure may be biased in any of numerous different ways that are currently known or that later become known, using biasing members other than springs. Further, if a spring is used, any of numerous different springs or combinations of springs may be used. In the illustrated embodiment, the closure 68 is a "shutter" closure that slides axially over the filling member 62 between the normally closed and open positions. However, as may be recognized by those of ordinary skill in the pertinent art based on the teachings herein, the closure may take any of numerous different configurations that are currently known, or that later become known, for performing the function of the closure as described herein.

Figure 9A:
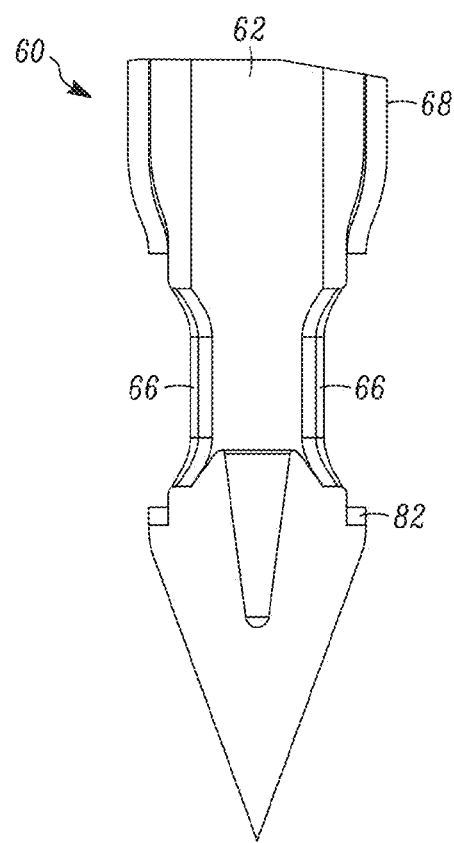
FIG. 9A is a side cross-sectional view of another embodiment of the distal end of the filling device of FIG. 6, including a seal over-molded to the stop surface formed at the tip of the filling member to facilitate forming a substantially fluid-tight or hermetic seal between the closure and filling device.
Figure 9B:
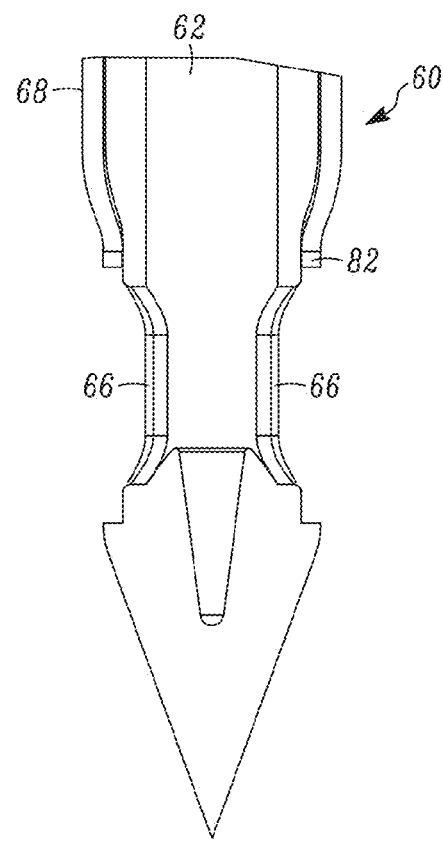
FIG. 9B is a side cross-sectional view of another embodiment of the distal end of the filling device of FIG. 6, including a seal over-molded to the distal end of the closure to facilitate forming a substantially fluid-tight or hermetic seal between the closure and filling device.

The closure 68 extends both annularly and axially about the filling member 62 and is slidably mounted on the filling member. The closure 68 includes an annular flange 76 adjacent to a proximal end thereof that is engageable with the biasing member 74 for biasing the closure in the direction from the second or open position toward the first or closed position. An opposing distal end 78 of the closure 68 is engageable with an annular stop surface 80 of the filling member tip 64 to stop the closure in the first or closed position. The distal end 78 of the closure 68 tapers inwardly to define a perimeter substantially flush with the perimeter of the stop surface 80 and adjacent portion of the filling member tip 64. As shown in FIGS. 9A and 9B, in alternative embodiments, the closure 68 (FIG. 9B) and/or the filling member tip 64 (FIG. 9A) includes an annular seal 82, between the distal end 78 of the closure and the tip 64 of the filling member, to further ensure the formation of a fluid-tight seal at the junction of the closure and filling member. In the embodiment of FIG. 9A, the seal 82 is o-ring shaped and is over-molded to the filling member tip 64. In the alternative embodiment of FIG. 9B, the o-ring shaped seal 82 is over-molded to the distal tip of the closure 68. As may be recognized by those of ordinary skill in the pertinent art based on the teachings herein, the seal may or may not be integral with the closure and may take the form of any of numerous different types of seals or sealing members that are currently known or that later become known, to facilitate the formation of a fluid-tight seal at the juncture of the closure and filling member. In the illustrated embodiment, the proximal end of the closure 68 is slidably received within the annular recess of the boss 72 of the filling member 62, and the biasing member 74 is located between the rear wall 84 of the boss 72 and the annular flange 76.

The flexible closure or shell 70 sealingly encloses the boss 72 of the filling member 62. In the illustrated embodiment, the flexible shell forms a bellows to allow the shell to axially expand when moving into the first or closed position (FIG. 7A) and to axially contract when moving into the second or open position (FIG. 7B). However, as may be recognized by those of ordinary skill in the pertinent art based on the teachings herein, the flexible shell may take any of numerous different configurations that are currently known, or that later become known, for performing the function of the shell as described herein. The flexible shell sealingly engages an outwardly projecting annular flange 86 of the boss 72 near the proximal end thereof, and sealingly engages an annular flange 88 of the closure 68 at the distal end thereof. In the illustrated embodiment, the closure annular flange 88 projects radially outwardly from an approximate mid-portion of the closure 68. The portion of the flexible shell 70 proximally adjacent to the boss annular flange 86 includes an annular recess that receives and retains the flange 76 and thus integral boss 72. The boss 72 includes corresponding venting holes 92 located adjacent to the rear wall 84 that are normally sealed by the valve 90. The venting holes 92 are in fluid communication with the interior recess of the boss 72. The interior of the boss 72 is in fluid communication with one or more annularly and axially extending channels formed between the closure 68 and filling member 62 which, as shown in FIG. 8C and FIG. 15C, are in fluid communication with a chamber to be filled when the closure is located in the second or open position. Thus, when the biasing member 74 is compressed upon movement of the closure from the first position to the second position, sufficient fluid pressure within the boss 72 (i.e., at or above the venting valve opening pressure) will cause the venting valve 90 to move radially outwardly relative to the holes 92 to thereby allow one-way venting of any such air or other gases into the ambient atmosphere. In addition, as described further below, during filling, any air or other gases (e.g., nitrogen) that are displaced from the chamber to be filled are allowed to vent through the channels between the closure and filling member and, in turn, through the venting valve 90. When the pressure equalizes, the valve 90 resiliently returns to its sealing position overlying and engaging the holes 92. In similar fashion, the venting valve 90 allows one-way venting of air or other gases through the venting holes 92, and into the shell 72 when a vacuum is present therein. As may be recognized by those of ordinary skill in the pertinent art based on the teachings herein, the venting valve may take the form of any of numerous integral or non-integral valves, that are currently known or that later becomes known, capable of performing the function of the venting valve as described herein.

In the illustrated embodiment, the filling device tip 64 is defined by a non-coring, conically-pointed tip; however, as may be recognized by those of ordinary skill in the pertinent art based on the teachings herein, the filling device tip may define any of numerous other tip configurations that are currently known, or that later become known, such as a trocar tip. In one configuration, the spring force of the biasing member 74 is sufficient to allow the filling device 60 to penetrate a septum of an opposing device while maintaining the closure 68 in the closed position during penetration of the closure through the septum and until the annular flange 88 of the closure engages an exterior surface of the septum (or other exterior or stop surface of the device to be filled) to cause relative movement of the closure and filling member against the bias of the biasing member 74 from the normally closed position to the open position and, in turn, expose the sterile filling device ports 66, 66 within the sterile device chamber.

A filling line attachment fitting 94 is formed on a proximal end of the filling member 62. In the illustrated embodiment, the attachment fitting 94 is a barbed fitting for attachment to a filling line (not shown). As may be recognized by those of ordinary skill in the pertinent art based on the teachings herein, any of numerous different types of fittings, connections or connectors that are currently known, or that later become known, equally may be employed for connecting the filling device to a filling or other type of line or conduit. For example, the proximal end of the filling device may define a male or a female connector for aseptically or sterile connecting to the other of the male or female connector attached to a filling line, as disclosed in U.S. Provisional Patent Application No. 61/641,248, filed May 1, 2012, entitled "Device for Connecting or Filling and Method" and similarly titled U.S. Provisional Patent Application No. 61/794,255, filed Mar. 15, 2013; U.S. Provisional Patent Application No. 61/635,258, filed Apr. 18, 2012, entitled "Self-Closing Connector;" and similarly titled U.S. Provisional Patent Application No. 61/625,663, filed Apr. 17, 2012, each of which is hereby expressly incorporated by reference in its entirety as part of the present disclosure as if fully set forth herein.

The filling device 60 may be used to aseptically or sterile fill fluids through the first penetrable septum 32 and into the chamber 11 of the device 10. As shown in FIG. 8A, FIG. 10B and FIG. 15A, prior to penetrating the first septum 32, and when the filling device tip 64 is exposed to the ambient atmosphere, the closure 68 is in the closed position sealing the ports 66 with respect to ambient atmosphere to thereby maintain the sterility of the ports and of the interior of the filling device. As shown in FIG. 8B and FIG. 15B, upon penetrating the first septum 32, the closure 68 remains interposed between the ports 66 and the first penetrable septum 32 to substantially prevent contact between the ports and the septum. When the ports 66 are located within the chamber 11, the bottom surface of the annular flange 88 of the closure engages the top surface of the first closure 22 and prevents further movement of the shutter closure 68 relative to the first closure 22. Further penetration of the filling device 60 into the chamber of the device 10 causes the filling member 62 and filling device tip 64 to slide relative to the shutter closure 68 against the bias of the biasing member 74 to, in turn, move the ports 66 to the open position. As the biasing member 74 is compressed with further movement of the shutter closure from the closed position to the open position, any fluid pressure within the shell 72 above of the venting valve opening pressure is allow to flow through the venting valve 90 into the ambient atmosphere. In the open position of FIG. 8C and FIG. 15C, the fluid or other substance within the filling device is permitted to flow through the open ports 66 and into the chamber 11. Any fluid within the chamber 11 that is displaced by the substance flowing into the chamber is allowed to vent through the channels formed between the shutter enclosure 68 and filling device 62 and, in turn, through the venting valve 90. Since the sterile ports 66 are never exposed to the ambient atmosphere throughout the filling process, the ports, interior of the filling device, and fluid flowing therethrough, are not contaminated and/or are maintained aseptic or sterile as the fluid is injected or otherwise filled into the chamber 11.

Figure 18A:
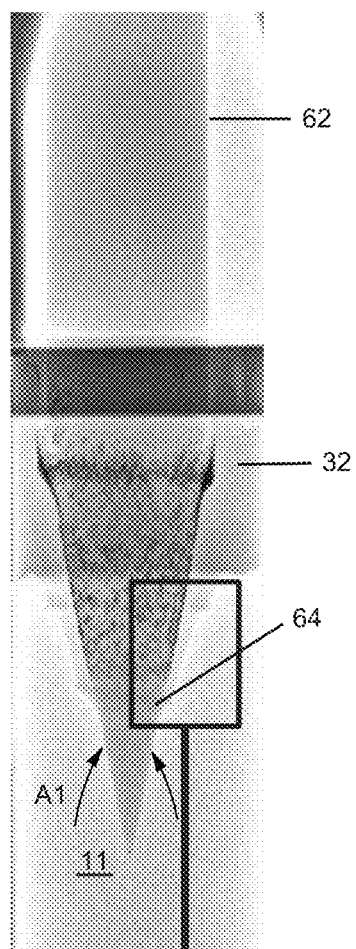
FIG. 18A is a photograph of the penetration tip of the injection member of the filling device during penetration of the elastic septum and illustrating the annular interface between the elastic septum and the injection member extending axially between a penetration point on an interior surface of the elastic septum in fluid communication with the sterile chamber, and an exterior surface of the septum engaging the injection member, and de-contaminating the injection member by friction between the elastic septum and injection member at the annular interface, and elongation of the elastic septum at the annular interface.
Figure 18B:
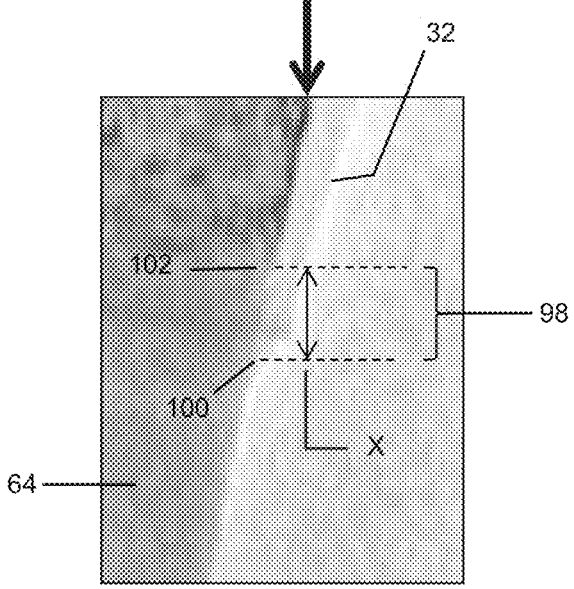
FIG. 18B is a partial, magnified view of FIG. 18A showing the annular interface in further detail.

In accordance with an embodiment, the method of sterile or aseptic filling of the device 10 comprises the following steps:

(a) Penetrating the elastic septum 32 of the device 10 with the tip 64 of the injection member 62. As described above, the device 10 defines a sealed, empty, sterile chamber 11 in fluid communication with the elastic septum 32;

(b) During the penetrating step, and as shown typically in FIGS. 18A and 18B, forming an annular interface 98 between the elastic septum 32 and the injection member 62 extending axially between a penetration point 100 on an interior surface of the elastic septum in fluid communication with the sterile chamber, and an exterior surface 102 of the septum engaging the injection member. Movement of at least one of the injection member 62 and elastic septum 32 relative to the other during the penetration step decontaminates the injection member 62, including the penetrating tip 64 and shutter closure 68 thereof, by at least one of (i) friction between the elastic septum 32 and injection member 62 at the annular interface 98, and (ii) elongation of the elastic septum 32 at the annular interface 98. In order to enhance the decontamination, the coefficient of friction of the septum-engaging surface of the injection member 62 is less than the coefficient of friction of the penetrated portion of the elastic septum 32.

(c) Introducing a substance, such as a vaccine, pharmaceutical injectable, liquid nutrition product, or other liquid, cream, gel, powder or gas, through the ports 66 of the injection member 62 and into the sterile chamber 11 of the device 10;

(d) Withdrawing the injection member 62 from the elastic septum 32;

(e) Allowing the elastic septum 32 to reseal itself at the penetration aperture resulting from withdrawal of the injection member 62; and (f) Maintaining the chamber 11 sterile throughout steps (a) through (e).

As shown best in FIGS. 18A and 18B, the annular interface 98 is defined by a portion of the penetrated elastic septum extending annularly about the injection member 62 substantially throughout an axial distance "X" extending between the interior and exterior points of contact 100 and 102, respectively, between the penetrated septum and injection member. In some embodiments, the axial distance is X at least about ½ mm, other embodiments at least about 1 mm, and in further embodiments at least about 1⅓ mm. In some embodiments, and as shown typically in FIGS. 18A and 18B, the annular interface 98 between the elastic septum and injection member defines a substantially inverted, frusto-conical shape.

In this embodiment, the penetrating step is performed in an ambient environment defining a level of contamination greater than about class 100 or ISO 5. Other embodiments comprise performing the above steps a) through e) in an ambient environment defining a level of contamination greater than about class 100 or ISO 5, and even in an ambient environment defining a level of contamination greater than about class 100 or ISO 5 and less than or equal to about class 100,000 or ISO 8.

In some embodiments, the de-contaminating of the injection member achieves at least approximately a 3 log reduction in bio-burden at the annular interface 98 between the elastic septum 32 and injection member 62, in other embodiments at least approximately a 5 log reduction in bio-burden at the annular interface 98 between the elastic septum and injection member, and in further embodiments at least approximately a 6 log reduction in bio-burden at the annular interface 98 between the elastic septum and injection member.

Figure 19:
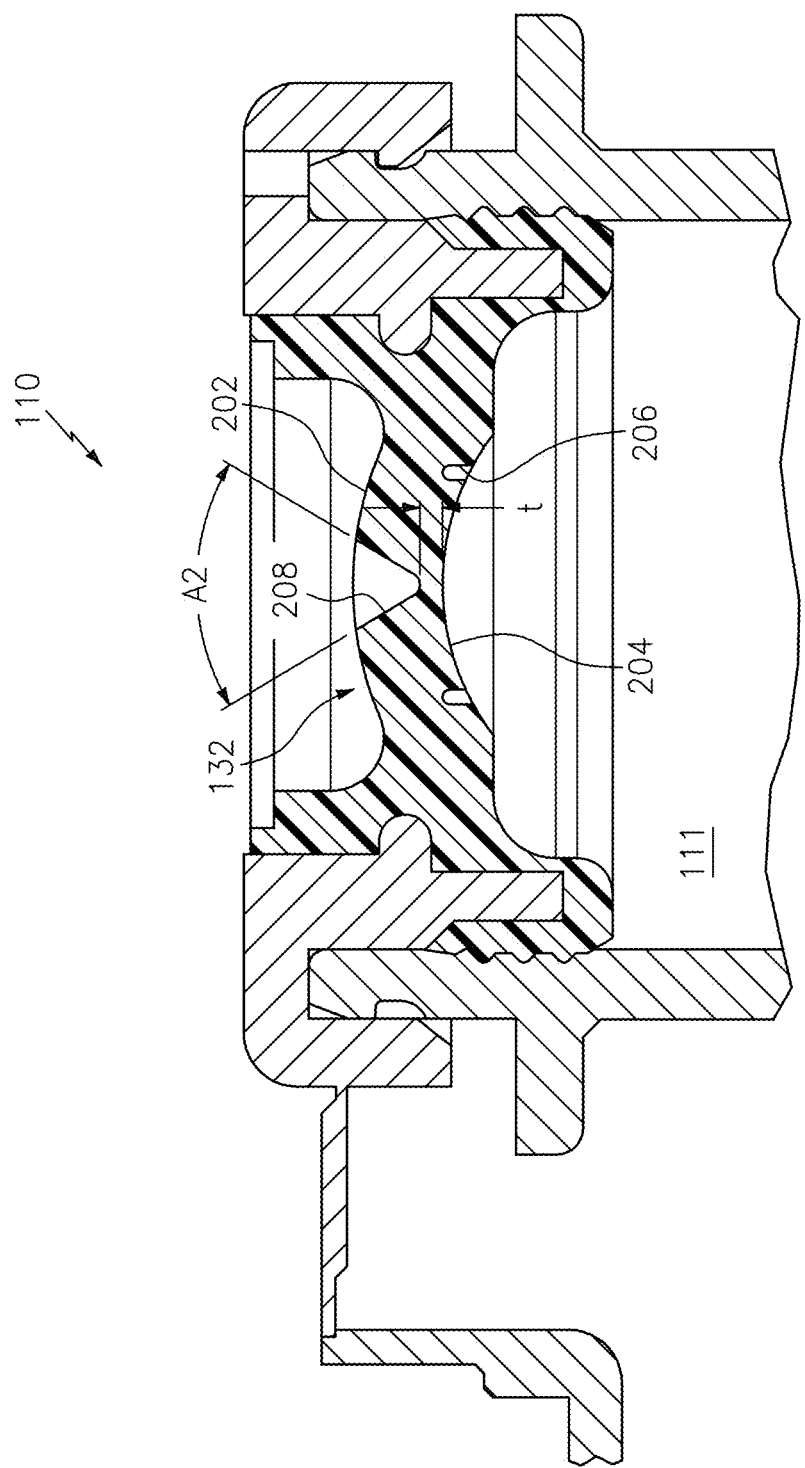
FIG. 19 is a cross-sectional view of another elastic septum including a v-shaped recess defining a reduced-thickness penetration zone, and a groove on the underside of the septum extending substantially annularly about and adjacent to the penetration zone.

In FIG. 19, an alternative embodiment of an elastic septum is indicated generally by the reference numeral 132. The elastic septum 132 is substantially similar to the elastic septum 32 described above, and therefore like reference numerals preceded by the numeral "1", or the numeral "2" instead of the numeral "1", are used to indicate like elements. As can be seen, the elastic septum 132 includes a penetration zone having an approximate dome-shape defining a substantially convex exterior surface 202, and a substantially concave interior surface 204 opposite the convex exterior surface. One advantage of the dome shape is that it enhances the pressure exerted by the elastic septum onto the injection member during the penetrating step. In some embodiments, the de-contaminating of the injection member 62 includes exerting pressure with the elastic septum 132 onto the injection member 62 at the annular interface between the elastic septum and injection member and, in turn, killing organisms at the interface. In some such embodiments, the exerting pressure on the injection member includes penetrating a substantially dome or convex shaped portion of the elastic septum as described in the exemplary embodiments herein. The interior surface 204 of the septum 132 defines a relatively recessed surface 206 extending substantially about the penetration zone. In the illustrated embodiment, the relatively recessed surface is a continuous, annular groove 206 that extends annularly about and adjacent or contiguous to the zone of penetration. One advantage of the annular groove or like structure is that it reduces the strain on the interior surface of the septum within the zone of penetration of the injection member during the penetrating step to, in turn, maximize the axial distance X of the annular interface 98.

The penetration zone of the elastic septum 132 includes a recess 208 formed therein defining a reduced thickness "t" of the elastic septum. During the penetration step described above, the tip 64 of the injection member 62 is received within the recess 208 and penetrates the septum at its penetration zone of reduced thickness "t". In the illustrated embodiment, the penetration zone recess 208 defines a substantially frusto-conical shape. As indicated above, the injection member 62 includes a penetrating tip 64 defining a first included angle "A1" (FIG. 18A), and the penetration zone recess 208 defines a second included angle "A2" that is substantially the same as the first included angle A1. In other embodiments, the injection member 62 includes a penetrating tip 64 defining a first included angle A1, and the penetration zone recess 208 defines a second included angle A2 that is greater than the first included angle A1. The interference between the included angle A1 of the penetrating tip 64 and included angle A2 of the penetration recess is selected to enhance the de-contamination of the injection member.

One advantage is that movement of at least one of the injection member 62 and elastic septum 32 relative to the other during penetration of the septum decontaminates the injection member 62, including the penetrating tip 64 and shutter closure 68 thereof, by at least one of (i) friction between the elastic septum 32 and injection member 62 at the annular interface 98, and (ii) elongation of the elastic septum 32 at the annular interface 98. Various factors can affect the de-contamination effect as hereinafter summarized.

The material of the elastic septum must impart a sufficient friction force to the injection member while nevertheless generating as few particles as possible during the penetration step. As a general matter, the higher the elongation of the material, the lower the number of cracks generated by friction and the greater the elongation of the septum material during the penetration step. In some embodiments, the elongation differential of the different components of the septum material is minimized to enhance the degree of elongation of the material prior to cracking during penetration. It also is generally desirable to use a septum material that exhibits relatively low, or minimal creep, in order to ensure relative rapid self-closure of the septum after withdrawal of the injection member therefrom to prevent exposure of the ambient environment to the sterile chamber. The septum material in some embodiments is molded, such as by injection, blow, compression molding, etc. In one embodiment, the elastic septum material is a silicone have a hardness within the range of about 1 shore A to about 100 shore A, such as within the range of about 20 shore A to about 80 shore A.

The configuration of the elastic septum also can affect the de-contamination effect. For example, a dome or convex/concave shape may be imparted to the penetration zone of the septum so that during penetration a radial compression is exerted by the septum onto the injection member, which in some embodiments is substantially maximized at the outset of the penetration of the septum by the injection member. Accordingly, the shape of the septum may be selected to maximize or enhance the radial compression exerted by the septum against the injection member during the penetration step.

In some embodiments, the crack needed to perforate the septum occurs at substantially the maximum elongation of the septum material, and is based on the desired stroke length of the injection member during the penetration step. Accordingly, based on the desired stroke length, the elongation of the septum prior to or at about the time of perforation of the septum is maximized.

With respect to the thickness of the septum, as a general matter, the longer the axial distance X of the annular interface between the elastic septum and injection member, the greater the de-contamination. Forming a recess in the penetration zone, such as the frusto-conical shaped recess described above, increases the axial length X of the annular interface, without significantly increasing the force required to penetrate the septum due to the reduced thickness of the septum at the penetration recess. The diameter and included angle of the penetration recess is determined based on, and balanced against, the diameter and included angle of the penetration tip of the injection member, to maximize the de-contamination effect by friction and elongation while maintaining an appropriate penetration force. The side wall of the penetration recess wipes and decontaminates the injection member, and the reduced thickness t of the septum is sufficient to de-contaminate the tip of the injection member not wiped upon passage through the penetration recess.

The ratio of the septum thickness to the outer diameter of the injection member also may be controlled to enhance the de-contamination effect. The internal pressure applied by the septum onto the injection member during penetration can be significant with respect to achieving the desired de-contamination of the injection member. For the minimum internal pressure to be applied, the injection member diameter must be large enough to be sufficiently wiped over the smallest septum thickness to be pierced. As a general matter, the larger the septum thickness for a given injection member outer diameter, the greater is the deformation of the septum and the longer the penetration stroke. The product of the internal pressure times the thickness of the penetration zone must be greater than a threshold required to de-contaminate the injection member in a certain level of decontamination in the ambient environment. The smaller the internal pressure, the greater should be the thickness of the septum. The axial distance of the annular interface is the minimum amount of de-contamination that occurs by elongation. When the injection member depresses the septum and creates the corresponding concavity (or frusto-conical shape) in the septum, the annular interface elongates until the elastomeric material reaches its maximum elongation before cracking. During this phase, the germ density initially high before elongation is reduced by the elongation effect alone.

As indicated above, in some embodiments the coefficient of friction of the septum is greater than the coefficient of friction of the injection member to enhance the friction at the interface and the resultant de-contaminating effect. Also, as a general matter, the greater the outer diameter of the injection member, the greater should be the thickness of the penetrated septum. Additionally, the hardness (or durometer) of the septum also affects the pressure applied by the septum onto the tip. In some embodiments, the durometer of the septum is within the range of about 20 Shore A to about 50 Shore A, such as within the range of about 25 Shore A to about 45 Shore A. In some such embodiments, the septum thickness is within the range of about ½ to about two times the largest diameter of the tip of the filling member.

The septum deformation after cracking and crack dilation also has an effect on the de-contamination effect. The strain on the inner surface of the septum tends to pull the pierced septum outwardly and, in turn, reduces the axial distance of the annular interface, shown typically as X in FIG. 18B. In some embodiments, the inner surface of the septum is configured to reduce the strain thereon and thus maximize the distance X of the annular interface. The greater is the distance X of the annular interface, the greater is the distance between the sterile chamber and the potentially contaminated exterior surface of the injection member, and thus the lower is the likelihood of any germs being pushed by the injection member through the septum and into the sterile chamber. The annular groove 206 or like recess formed on the interior surface of the septum adjacent to the zone of penetration reduces the strain on the interior surface during penetration thereof by the injection member. During penetration, the groove dilates, and the strain on the inner edge or wall of the groove is reduced to, in turn, allow greater elongation of septum by the injection member and thus a larger axial distance X of the annular interface.

The material of the filling member 62 and the septum 32 also may be selected to enhance the decontamination effect. The present inventor has determined that the use of a plastic filling member provides the appropriate friction coefficient range to enhance the effect of decontamination by friction force. Advantageously, the plastic material is also easier to mold, and thus easier to manufacture and assemble. The present inventor also has determined that a septum made of a homogeneous elastic material defining a substantially homogeneous density will enhance the decontamination effect. In some embodiments, the filling or injection member is formed of plastic, such as any of numerous different thermoplastics, including the liquid crystal polymers (LCP) that are highly crystalline, thermotropic (melt-orienting) thermoplastics and sold under the trademark Vectra™ by Celanese Corporation, or graphene. In some such embodiments, the elastic septum is made of silicone. In other embodiments, the elastic septum is made of a vulcanized rubber or a thermoplastic. However, as may be recognized by those of ordinary skill in the pertinent art based on the teachings herein, the filling member and septum may be made of any of numerous different materials that are currently known, or that later become known, to perform the functions of the filling member and septum disclosed herein.

The configuration of the filling member itself also can enhance the decontamination effect. The included angle of the tip of the filling member affects the progressively increasing thickness of the tip, and the diameter of the filling device, i.e., the outer diameter of the shutter closure. As the filling member penetrates through the elastic septum, the internal pressure applied by the septum onto the tip, and thereafter onto a portion of the rigid closure increases proportionally to the progressively increasing tip diameter, resulting from the included angle of the tip. In some embodiments, the included angle of the tip of the piercing member is within the range of about 20 degrees to about 40 degrees, and such as about 30 degrees.

The present inventor has determined that the wiping effect on a filling member tip by a septum having properties as aforementioned may achieve at least approximately a 3 log reduction in bio-burden, which is about the reduction achieved by known UV pulse (5 second) sterilization techniques, and up to approximately a 6 log reduction in bio-burden. Another advantage is that the filling device may sterile fill a substance into the device without the need to decontaminate the septum of the device or the tip of the filling device prior to filling. The combination of the maintained sterility of the ports and interior of the filling device, as well as the decontamination effect provided by the elastic septum effectively sterilize the tip of the filling member upon penetration of the filling member through the septum. Therefore, one advantage of such embodiments is that it allows substantially sterile filling of fluids within a non-aseptic, non-sterile or relatively low sterility assurance level ("SAL") environment, such as a controlled, non-classified environment. Such an environment may define a level of contamination greater than about class 100 or ISO 5 and less than or equal to about class 100,000 or ISO 8. In such a controlled, non-classified environment, an operator may wear a lab coat, hair net and gloves, and if desired, the filling device may be installed in a room with closed room door access. However, there is no need for a clean room, isolator, or any of the other numerous controls and requirements required by the prior art sterile or aseptic filling methods and systems.

As shown in FIG. 15D, after the chamber 11 is filled as desired, the filling device 60 is withdrawn from the first septum 32. As the filling device is withdrawn, the biasing member 74 biases the rigid closure 68 downwardly or in the direction of the septum 32. Therefore, as the filling member 62 is withdrawn, it is moved axially relative to the shutter closure 68 to, in turn, move the ports 66 into the closed position behind the closure. The shutter closure 68 is configured to substantially prevent contact between the filling device eyes or ports 66, and as can be seen, the sliding shutter or closure is closed over the filling device eyes or ports prior to their passage through the septum and/or withdrawal therefrom. When the distal end 78 of the closure 68 sealingly reengages the stop surface 80 of the filling device tip 64, the closure is in the closed position, and is maintained in the closed position by the downward force or bias of the biasing member 74. Thus, during, upon, and before, withdrawal of the filling device 60 from the first septum 32, the closure 68 sealingly closes the ports 66 and prevents contamination of the ports or interior of the filling device.

As indicated above, the first septum 32 is engineered in a manner known to those of ordinary skill in the pertinent art to self-close and thereby ensure that the head loss left by the residual filling device injection aperture 96 after the tip of the filling device is withdrawn substantially prevents fluid ingress therethrough. Thereafter, as shown in FIG. 4, the second closure portion 24 is moved from the first position, and snaps into the second position, and the unpenetrated second septum 34 overlies and seals the injection aperture 96 in the first septum 32 from the ambient atmosphere. This forms a filled, sealed device as shown in FIG. 10C, FIGS. 14, FIG. 16A, and FIG. 17A. Prior to moving the second closure 24 from the first position to the second position, the exterior surface of the first closure 22 and/or the interior surface of the second closure 24 may be sterilized, such as is shown in the example of FIG. 16A, in order to prevent any contaminants from between trapped between the first and second septums 32 and 34, respectively, after closure of the second closure to the first closure. Sterilization of these surfaces may be performed in any of numerous different ways that are currently known, or that later become known, including without limitation, by the application of radiation thereto, such as e-beam, laser or UV radiation, by the application of a fluid steriliant, such as vaporized hydrogen peroxide ("VHP") or nitric oxide ("NO"), or by heated gas.

Figure 17A:
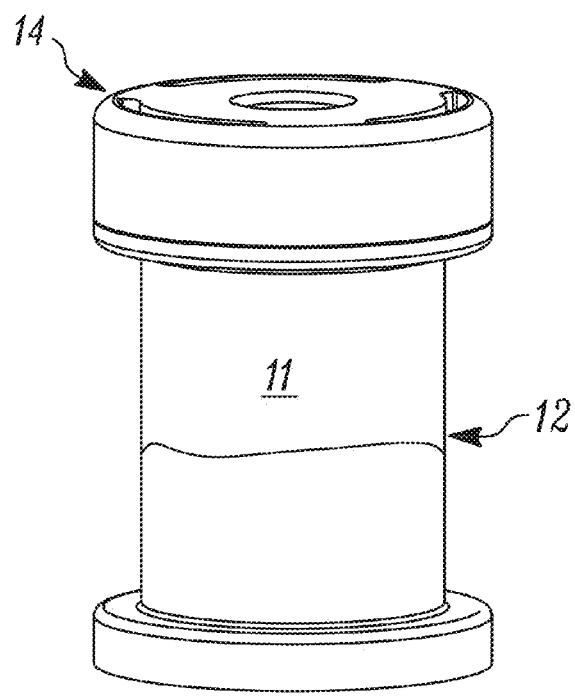
FIG. 17A is a side view of the filled device of FIG. 10A ready for sampling of substance in the chamber.
Figure 17B:
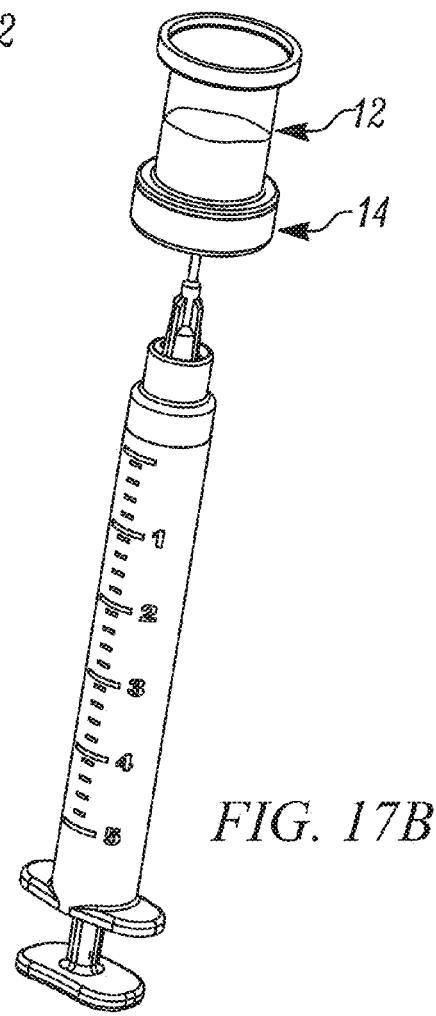
FIG. 17B is a side view of the filled device of FIG. 17A with a needle piercing the second closure into the chamber to permit sampling of substance from the chamber.

If desired, a further closure may be applied over the second closure 24 and/or second septum 34, such as an adhesive-backed foil layer that overlies the second septum 24 and is adhesively attached to the second septum or second closure, to provide an additional barrier such as to prevent moisture-vapor transmission ("MVT"). When ready for use, the adhesive-back foil layer or other additional MVT barrier may be manually engaged and removed to expose the second septum. Then, as shown in FIG. 10D and FIG. 17B, a syringe needle or like withdrawal device may be pierced through the first and second septums and placed into fluid communication with the interior chamber 11 and the fluid or other substance therein to withdraw the fluid or other substance from the chamber and into the syringe to, for example, inject the withdrawn substance into a person, patient or other subject. In some embodiments, the first and second septums may be pierced one or more times as desired to withdraw substance from the chamber 11 until the chamber is empty as shown in FIG. 10E.

In other embodiments, the second closure is initially a separate piece and is not connected to the first closure as disclosed in the following co-pending patent application which is hereby expressly incorporated by reference in its entirety as part of the present disclosure: Co-pending U.S. Provisional Application entitled "Device With Penetrable Septum, Filling Needle and Penetrable Closure, and Related Method" filed on even date herewith. After the first closure is pierced and the device is filled with a substance, the second closure is then fixedly secured, such as by a snap fit as described above, to the first closure to sealingly engage the first and second septums, and seal the resulting penetration aperture in the first septum. The second closure can be pre-sterilized prior to assembly, or can be surface sterilized as described above prior to assembly to the first closure. The second closure can be automatically assembled to the first closure with any of numerous different assembly devices that are currently known, or that later become known, such as a pick and place robotic assembly device, or other suitable fixture that can automatically assemble the second closure to the first closure. A closure assembly station can be located downstream of the needle penetration and filling station to assemble the second closure to the first closure upon or following withdrawal of the filling needle from the first closure.

In other embodiments, the second closure is eliminated, and the resulting penetration aperture in the elastic septum is resealed in any of numerous different ways that are currently known, or that later become known, such as by resealing the resulting penetration aperture with a liquid sealant, a thermal seal, and/or a chemical seal. Some embodiments further comprise transmitting radiation onto the resulting penetration aperture to effect or further effectuate the seal.

In another embodiment, the devices to be sterile filled are cartridges wherein each cartridge includes a sealed, empty, sterile chamber, and an elastic septum in fluid communication with the sterile chamber. The filling device includes one or more filling members, and each filling member is connected in fluid communication with a respective source of substance, product or product component to be filled therethrough. A computerized controller controls the respective filling devices to fill into each cartridge one or more respective components, a label is printed to indicate the component(s) filled into the respective cartridge and any other desired information, and the label is applied to the respective filled cartridge. The resulting penetration aperture or apertures in the elastic septum are resealed by a mechanical seal, a liquid sealant, a thermal seal, and/or a chemical seal. If desired, radiation may be transmitted onto the resulting penetration aperture to effect or further effectuate the seal. Each cartridge may include a sterile connector for purposes of withdrawing the component or components filled into the sterile chamber. Exemplary such sterile connectors are disclosed in the following co-pending patent applications, each of which is hereby expressly incorporated by reference as part of the present disclosure: U.S. patent application Ser. No. 13/080,537, filed Apr. 5, 2011, entitled "Aseptic Connector with Deflectable Ring of Concern and Method", which claims the benefit of similarly titled U.S. Provisional Application No. 61/320,857, filed Apr. 5, 2010; U.S. patent application Ser. No. 13/874,839, filed Apr. 17, 2013, entitled "Device for Connecting or Filling and Method", which claims the benefit of similarly titled U.S. Provisional Patent Application No. 61/641,248, filed May 1, 2012, and similarly titled U.S. Provisional Patent Application No. 61/794, 255, filed Mar. 15, 2013; and U.S. patent application Ser. No. 13/864,919, filed Apr. 17, 2013, entitled "Self-Closing Connector", which claims the benefit of similarly titled U.S.

Provisional Patent Application No. 61/635,258, filed Apr. 18, 2012, and similarly titled U.S. Provisional Patent Application No. 61/625,663, filed Apr. 17, 2012, each of which is hereby expressly incorporated by reference in its entirety as part of the present disclosure as if fully set forth herein.

Turning now to FIGS. 20-23, an apparatus 300 for filling and resealing sealed containers or other devices is shown. The apparatus described below can provide small-scale sterile filling, for example: for pharmaceutical and biotechnology research and development, university teaching, research, and development, clinical trials, analytical laboratories; at pharmacies, hospitals, doctor's offices, extended care facilities, and/or emergency and rescue operation areas for on-demand dispensing and production for customers and patients; at food processing plants; at facilities for manufacturing and formulation trials, research, and production; and can be used in emerging markets and countries where large scale production may not be feasible and/or cost-effective.

Apparatus 300 is capable, in at least some embodiments, of employing the filling process described above, using device 10 and filling device 60. However, those skilled in the art will appreciate that other types of devices and containers and/or filling devices and needles can be used in apparatus 300. For example, container 301 can be formed from glass and/or plastic and can be of various shapes, sizes, and dimensions, including, for example, vials, tubes, pouches, bottles, etc., with volumetric dimensions of about 2 ml up to about 500 ml. In some embodiments developed by the inventor, the apparatus 300 can sterile fill up to about 200 units per hour. However, as should be understood by those of ordinary skill in the art, the preceding listed devices, sizes, and unit output are merely exemplary, and other devices and sizes that are currently known or will become known can be filled, and the filling apparatus can be configured as suitable for a particular device and output requirement.

Figure 20:
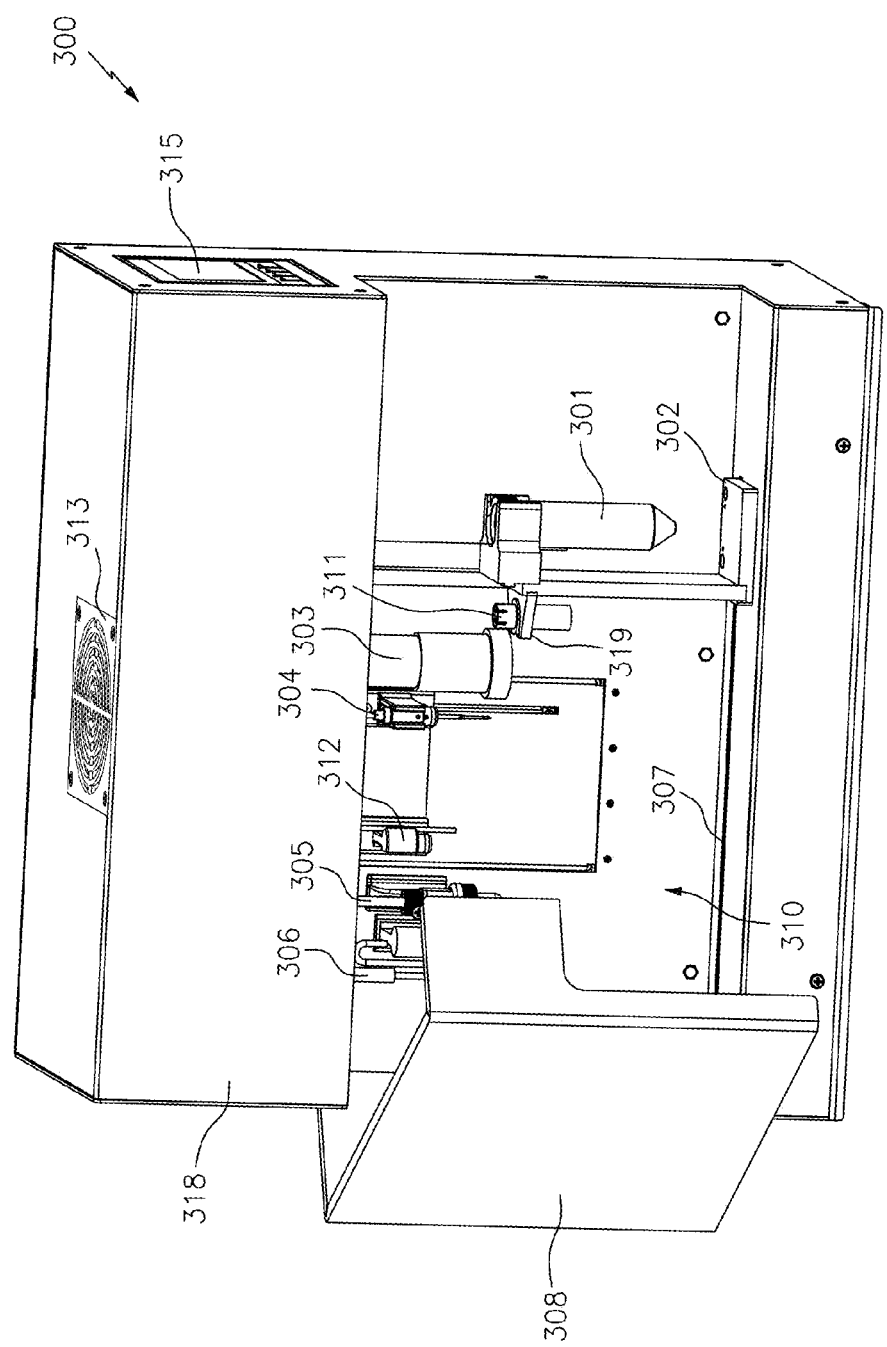
FIG. 20 is a front perspective view of an apparatus for filling and resealing sealed containers.

FIG. 20 shows a perspective front view of apparatus 300 that is configured to fill and reseal a container 301. The apparatus 300 defines a filling or processing space 310 in which the filling and resealing process is performed. Container 301, as shown, is held by a movable support 302 during the filling and resealing process. The support is configured to hold the container 301 substantially without moving relative to the support, especially in a vertical direction, during the filling and resealing process. The support is movable within the processing space 310 between the various steps, and/or stations of the apparatus 300, of the filling and resealing process, as further described below.

Support 302 can be moved during the filling and resealing process manually or in an automated process by a servo-motor or other electric motor drive. In other embodiments, other mechanical and/or electrical mechanisms are employed to convey the container 301 through the apparatus 300 on support 302. For example, in other embodiments, the movable support 302 is transported by a belt drive, gears, a belt-driven carriage, a screw motor, a conveyor, a loop-conveyor, is magnetically-driven, hydraulically-driven, pneumatically-driven, hand crank driven, or operated by any other mechanism that is currently known or that later become known. Furthermore, the drive mechanism and support 302 is configured to stop the support 302 at specific points as it is moved, and securely holds or locks the support, and thus the container 301, at the desired position to prevent undesired movement of the container 301 or support 302. The movement of the support 302 is controlled, by electrical and/or computer components connected thereto that are contained within apparatus 300 in a manner that should be understood by those of ordinary skill in the art. Control panel 315 provides a control interface between a user and the apparatus 300 to control components, by which the user can operate the apparatus. In the illustrated embodiment, to move container 301 through the apparatus 300 and the filling or processing space 310 thereof, the support 302 is mounted on a bi-directional conveyer that runs along a track 307, such as a channel or path, and a motorized mechanism moves the conveyer, and consequently the support 302 attached thereto, and the container 301 mounted thereon, in a first direction through the apparatus 300, to fill and then seal the container 301, and then move the support 302 back in a second direction opposite to the first direction, to remove the container 301 to outside the processing space 310, where the user can unmount the filled and sealed container. In other embodiments, the user manually moves support 302, and/or container 301 into the processing space 310, to the various stations in the processing space, to fill and then seal container 301, as described below, and then out of the processing space 310 to remove the container from the support 302.

The filling process described below takes place within the processing space 310 of apparatus 300. Processing space 310 is partially defined by the housing 318 of the apparatus 300, and further defined by a hinged door 308 that, in the closed position encloses the components of the apparatus 300 that interact with the container 301, and in the open position, as seen in FIG. 20, allows access to the processing space 310 and components therein. Door 308 is an opaque plastic material, but in other embodiments is plastic, glass, acrylic, and/or composite material that is transparent or opaque, or formed from other suitable materials as will be appreciated by those of ordinary skill on the art. Further, the door 308 in some such embodiments is of a material and/or coated with appropriate coatings to prevent ultraviolet radiation, laser radiation, ebeam radiation, and/or other types of radiation from passing therethrough when the door is closed to protect the user. In addition to providing a protective barrier for radiation, door 308 allows for a user or operator of apparatus 300 to access the components that are within the processing space 310, including for maintenance and repair, and/or to provide access to the container 301 once it is conveyed into the processing space 310 on support 302. Further, although shown as a hinged door 308, the door of apparatus 300 in other embodiments is a sliding door or a removable door or panel that, when attached to apparatus 300, defines the processing space 310.

To begin the process of using apparatus 300, it is turned on, to provide electrical power to the components and initialize the electronic/computer components. The user then operates the apparatus via the control panel 315. The user removably mounts a removable filling device 304, such as a closed needle 60 as described above, an open-eye needle, or any other type of suitable filling device into apparatus as shown in FIG. 20. In the illustrated embodiment, the filling device 304 is a closed needle of the type described above. The filling device 304 is connected to a source of substance to be filled into the container 301, as further described below.

In this embodiment, the needle 304 includes a removable cap 311 extending over the tip of the needle 304 to help keep contaminants off the filling device 304 and help prevent accidental needle sticks to the user. When the user initiates the filling process, the cap 311 is removed from needle 304 to expose the piercing tip of the filling device, such as the illustrated needle. As seen in the drawing, the support 302 includes a cap grip 319. In the cap 311 removal process, the support 302 is transported into the processing space 310 so that the cap grip 319 is aligned directly below the needle 304 and cap 311. The filling device 304 is then moved downwardly in a manner more fully described below, until the cap 311 is engaged in the cap grip 319 as seen in FIG. 20. The needle 304 is then retracted upward, disengaging the cap 311 from the filling device 304. In the illustrated embodiment, the filling device 304 and cap 311 define a snap on/off engagement, for repeatable detachment and attachment of the cap 311 and filling device 304. However, as should be appreciated by those of ordinary skill in the art, other types of mechanisms allowing detachment and reattachment of the cap 311 to the filling device 304 are used in further embodiments.

Figure 21:
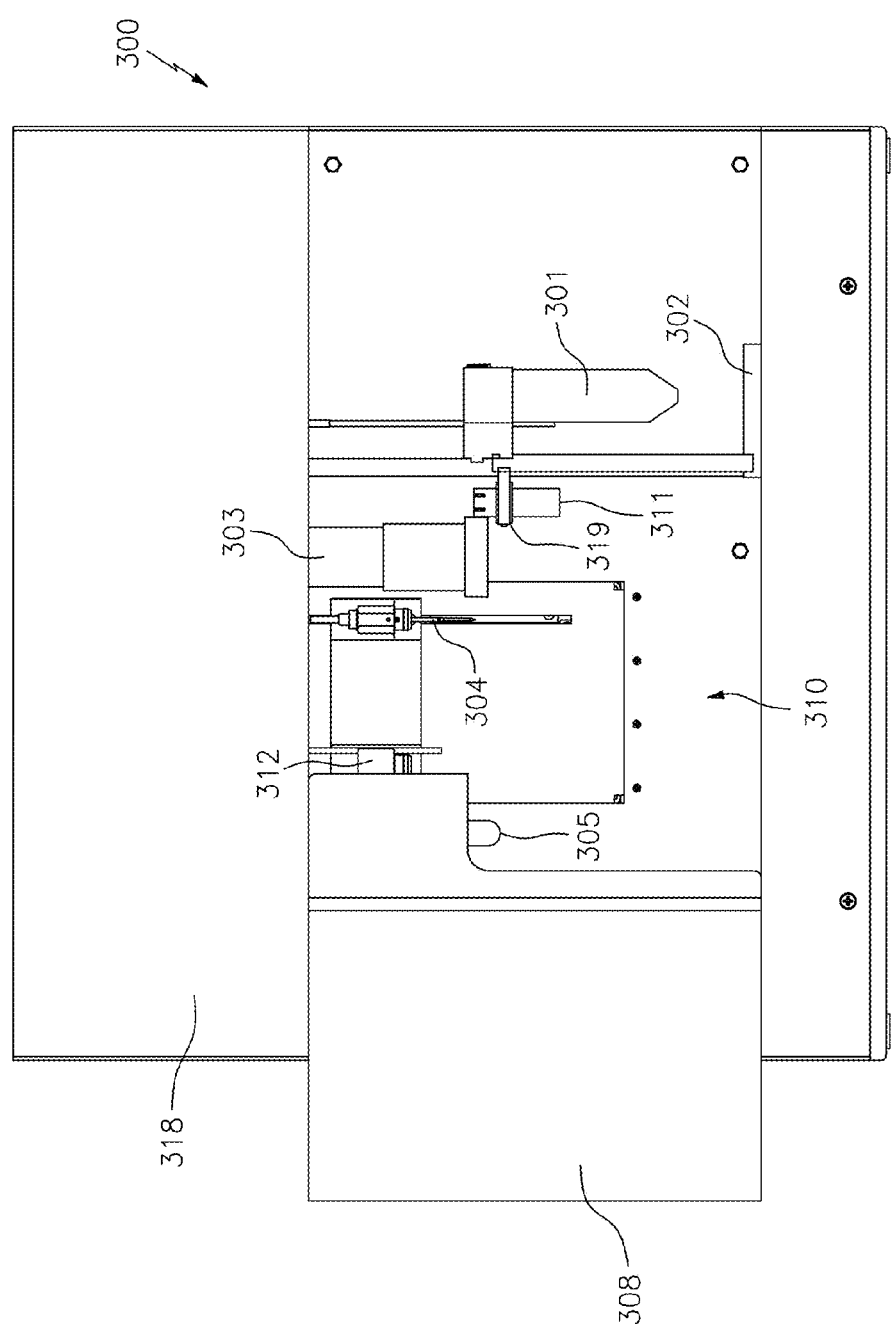
FIG. 21 is a front elevational view of the apparatus of FIG. 20.

As seen in FIGS. 20 and 21, the cap 311 remains mounted in the cap grip 319 of support 302 during the remainder of the filling process.

Alternatively, the cap 311 is stored on cap holder 312 during the filling process. In this embodiment the holder 302 is moved further into the processing space 310 (to the left in FIG. 20) until the cap 311 is aligned directly below the cap holder 312. The cap holder 312 is then moved downwardly until it engages and releasably retains the cap 311. The cap holder 312 is then retracted upward with the cap 311 engaged to it, removing the cap 311 upwardly out of the cap grip 319. The cap 311 is thus engaged by the cap holder 312 in a storage position during the filling and sealing process. As illustrated, the cap 311 and cap holder 312 define a snap on/off engagement, for repeatable detachment and attachment of the cap 311 and filling device 304. However, as should be appreciated by those of ordinary skill in the art, other types of mechanisms allowing attachment and detachment of the cap 311 to the cap holder 312 are used in further embodiments.

After the cap 311 is removed from the filling device 304, the support 302 will then move back out of the processing space 310, to its original position (far right in FIG. 20). This process of cap removal is an automated process initiated by the user via the control panel 315, but in other embodiments, the cap 312 is manually removed and stored by the user.

Next, a user installs, mounts, and/or removably attaches a vial or other container 301 onto the support 302 as seen in FIG. 20, to be filled. Once the container 301 is mounted to support 302, the filling and resealing process is initiated by the user via the control panel 315. The filling process is then performed in a fully automated manner by the electronic components of the apparatus 300. In other embodiments, the filling process is performed manually, and/or with a combination of automatic and manual steps.

During the filling and resealing process, container 301 is moved on the support 302 to a series of positions or stations, each performing a different step in the process. The container 301 is first moved to a decontamination and/or sanitizing station, underneath a decontamination and/or sanitizing device 303 that is configured to decontaminate and/or sanitize the top of the container 301, which as illustrated includes a penetrable septum, as described above. Sanitization and/or decontamination of the top of the container 301, including the septum is then performed using ultraviolet (UV) radiation emitted by the sanitizing device 303 onto the container 301 for a sufficient time to adequately sanitizing the septum. Sanitizing device 303 is a low-power UV-emitting LED (light emitting diode). Other embodiments use other types of UV-emitting devices, e.g., a UV-emitting light bulb, a UV laser, etc.

It should be appreciated by those of ordinary skill in the art that in other embodiments the sanitizing device 303 is a different type of decontamination device that is currently known, or that later becomes known, such as radiation emitting devices (e.g., gamma, ebeam, thermal laser or other type of sterilizing radiation), or a fluid sterilant applicator (e.g, vaporized hydrogen peroxide or nitric oxide). In alternative embodiments, the container 301 is sterilized, sanitized, and/or decontaminated prior to being placed in apparatus 300, as described above, such that the apparatus 300 does not include the sanitizing device 303.

After the container 301 is sanitized, the container 301 is moved to a filling station, including the filling device 304, to be filled as described above. For example, the support 302 and container 301 are moved to a position underneath the filling device 304. The filling device 304 illustrated in FIGS. 20 and 21 is a closed, non-coring needle, but in other embodiments is another type of needle or injection member. The filling device 304 is moved downward into contact with the septum of the container 301 by a servo-motor, or in alternative embodiments, another mechanical and/or electrical mechanism, for example, a manual lever or electric motor, and punctures the septum. The filling device 304 then passes through the septum and forms an aperture therethrough. Once the filling device 304 punctures the septum and passes therethrough into the chamber of the device 301, a port or opening of the filling device 304 will be in fluid communication with the chamber of container 301 and can dispense substance into the chamber. Substance is pumped by the apparatus 300 and into and through the filling device 304 and into the chamber of the container 301 by a peristaltic pump (not shown) contained within apparatus 300. The pump pumps the substance to be filled from a source of the substance, discussed further below. Those skilled in the art will appreciate that other types of pumps are employed to pump substance through the filling device 304 and into the chamber of the container 301 in alternative embodiments.

Control panel 315 is used to program and/or set a specific and/or precise amount or volume of substance that is to be dispensed into the chamber of the container 301. The apparatus 300 includes microprocessors, electrical mechanisms, and/or other control devices and functions to control or meter the flow of substance through the filling device 304. In an exemplary embodiment, the apparatus 300 controls the flow volume by operating the pump for a predetermined interval of time that will pump the programmed amount. In other embodiments, flow amount is controlled in alternative manners that are currently known or may become known. In this manner, the fill volume of the container 301 can be programmed by the user via the control panel 315, e.g., about 2 ml up to about 500 ml, and the apparatus 300 will pump the programmed amount into the container.

After the container 301 is filled, the filling device 304 is retracted or removed from the septum of the container 301, i.e., moved upward back into the position shown in FIG. 20. As described above, where the septum is resilient or self-closing, the aperture formed in the septum will close in a manner sufficient to substantially prevent leakage or passage of contaminants through the aperture until resealing can be performed.

To reseal the container, the container 301 is next moved or conveyed by the support 302 within the processing space 310 to a sealing station that includes a liquid sealant dispenser 305 and then a sealer device 306. First, the container 301 is conveyed by support 302 to the sealant dispenser 305. Sealant dispenser 305 is configured to dispense a liquid sealant onto the septum of the container 301 to cover and/or seal the aperture that was formed during the filling step by the filling device 304. The sealant is supplied from a cartridge stored within the apparatus 300, which is replaceable/refillable from an access panel on the back side and/or top of the apparatus 300, similar in function to a printer cartridge.

After the liquid sealant is dispensed to cover the aperture, the support 302 conveys the container 301 to the sealer device 306 that is configured to cure the dispensed sealant and seal the aperture, thereby forming a hermetic, sanitary sealed container 301 with a substance stored therein. In the illustrated embodiment, the sealant dispenser 305 deposits a UV curable liquid sealant drop onto the septum to cover the aperture, and then the sealer device 306 applies ultraviolet radiation to the liquid sealant drop using a UV LED (or in alternative embodiments, another UV source) to cure the sealant and form a hermetic seal, for example, as disclosed in co-pending U.S. patent application Ser. No. 13/745,721, filed Jan. 18, 2013, entitled "Device with Co-Molded Closure, One-Way Valve, Variable-Volume Storage Chamber and Anti-Spritz Feature and Related Method," which is hereby expressly incorporated by reference in its entirety as part of the present disclosure.

Alternatively, other embodiments utilize different methods of sealing the filling device aperture formed in the septum. These include a mechanical seal, a thermal seal, and/or a chemical seal. In embodiments utilizing a mechanical seal, the sealant dispenser 305, 306 is omitted from apparatus 300. Examples of mechanical seals and methods are disclosed, for example, in U.S. patent application Ser. No. 13/080,537, filed Mar. 14, 2014, entitled "Device with Sliding Stopper and Related Method," which claims the benefit of similarly titled U.S. Provisional Application No. 61/799,423, filed Mar. 15, 2013, which are hereby incorporated by reference in their entireties as part of the present disclosure. In some such embodiments, the sealer 306 is formed as a tongue or other pressure application mechanism that pushes a stopper or other seal into place over the aperture to form a hermetic seal between the container 301 chamber and the ambient atmosphere as described, for example, in the above-listed patents and patent applications.

In other embodiments, the septum of container 301 is a heat-resealable septum, and is resealed by the application of laser radiation or energy, to hermetically seal the filled substance within the chamber of container 301 from the ambient atmosphere. Such embodiments do not include a sealant dispenser 305, and sealant device 306 contains one more laser devices. Such resealing is performed, for example, in accordance with the teachings of any of the following patents and patent applications, each of which is hereby expressly incorporated by reference in its entirety as part of the present disclosure: U.S. patent application Ser. No. 12/254,789, filed Oct. 20, 2008, entitled "Container Having a Closure and Removable Resealable Stopper for Sealing a Substance Therein and Related Method," which, in turn, claims the benefit of U.S. Patent Application Ser. No. 60/981,107, filed Oct. 18, 2007, entitled "Container Having a Closure and Removable Resealable Stopper for Sealing a Substance Therein;" U.S. patent application Ser. No. 12/245,678, filed Oct. 3, 2008, entitled "Apparatus For Formulating and Aseptically Filling Liquid Products," and U.S. patent application Ser. No. 12/245,681, filed Oct. 3, 2008, entitled "Method For Formulating and Aseptically Filling Liquid Products," which, in turn, claim the benefit of U.S. Patent Application Ser. No. 60/997,675, filed Oct. 4, 2007, entitled "Apparatus and Method for Formulating and Aseptically Filling Liquid Products;" U.S. patent application Ser. No. 12/875,440, filed Sep. 3, 2010, entitled "Device with Needle Penetrable and Laser Resealable Portion and Related Method," now U.S. Pat. No. 7,980,276, which is a divisional of U.S. patent application Ser. No. 12/371,386, filed Feb. 13, 2009, entitled "Device with Needle Penetrable and Laser Resealable Portion," now U.S. Pat. No. 7,810,529, which is a continuation of U.S. patent application Ser. No. 11/949,087, filed Dec. 3, 2007, entitled "Device with Needle Penetrable and Laser Resealable Portion and Related Method," now U.S. Pat. No. 7,490,639, which is a continuation of similarly titled U.S. patent application Ser. No. 11/879,485, filed Jul. 16, 2007, now U.S. Pat. No. 7,445,033, which is a continuation of similarly titled U.S. patent application Ser. No. 11/408,704, filed Apr. 21, 2006, now U.S. Pat. No. 7,243,689, which is a continuation of U.S. patent application Ser. No. 10/766,172, filed Jan. 28, 2004, entitled "Medicament Vial Having a Heat-Sealable Cap, and Apparatus and Method for Filling the Vial," now U.S. Pat. No. 7,032,631, which is a continuation-in-part of similarly titled U.S. patent application Ser. No. 10/694,364, filed Oct. 27, 2003, now U.S. Pat. No. 6,805,170 which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application Ser. No. 60/182,139, filed Feb. 11, 2000, and similarly titled U.S. Provisional Patent Application Ser. No. 60/443,526, filed Jan. 28, 2003, and similarly titled U.S. Provisional Patent Application Ser. No. 60/484,204, filed Jun. 30, 2003; U.S. patent application Ser. No. 13/193,662, filed Jul. 29, 2011, entitled "Sealed Contained and Method of Filling and Resealing Same," which is a continuation of U.S. patent application Ser. No. 12/791,629, filed Jun. 1, 2010, entitled "Sealed Containers and Methods of Making and Filling Same," now U.S. Pat. No. 7,992,597, which is a divisional of U.S. patent application Ser. No. 11/515,162, filed Sep. 1, 2006, entitled "Sealed Containers and Methods of Making and Filling Same," now U.S. Pat. No. 7,726,352, which is a continuation of U.S. patent application Ser. No. 10/655,455, filed Sep. 3, 2003, entitled "Sealed Containers and Methods of Making and Filling Same," now U.S. Pat. No. 7,100,646, which is a continuation-in-part of U.S. patent application Ser. No. 10/393,966, filed Mar. 21, 2003, entitled "Medicament Vial Having A Heat-Sealable Cap, and Apparatus and Method For Filling The Vial," now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application Ser. No. 60/182,139, filed on Feb. 11, 2000, and U.S. Provisional Patent Application Ser. No. 60/408,068, filed Sep. 3, 2002, entitled "Sealed Containers and Methods Of Making and Filling Same;" U.S. patent application Ser. No. 12/627,655, filed Nov. 30, 2009, entitled "Adjustable Needle Filling and Laser Sealing Apparatus and Method," now U.S. Pat. No. 8,096,333, which is a continuation of similarly titled U.S. patent application Ser. No. 10/983,178, filed Nov. 5, 2004, which, in turn, claims the benefit of U.S. Provisional Patent Application Ser. No. 60/518,267, filed Nov. 7, 2003, entitled "Needle Filling and Laser Sealing Station," and similarly titled U.S. Provisional Patent Application Ser. No. 60/518,685, filed Nov. 10, 2003; U.S. patent application Ser. No. 11/901,467, filed Sep. 17, 2007 entitled "Apparatus and Method for Needle Filling and Laser Resealing," which is a continuation of similarly titled U.S. patent application Ser.

No. 11/510,961 filed Aug. 28, 2006, now U.S. Pat. No. 7,270,158, which is a continuation of similarly titled U.S. patent application Ser. No. 11/070,440, filed Mar. 2, 2005; now U.S. Pat. No. 7,096,896, which, in turn, claims the benefit of U.S. Provisional Patent Application Ser. No. 60/550,805, filed Mar. 5, 2004, entitled 'Apparatus for Needle Filling and Laser Resealing;" U.S. patent application Ser. No. 12/768,885, filed Apr. 28, 2010, entitled "Apparatus for Molding and Assembling Containers with Stoppers and Filling Same," now U.S. Pat. No. 7,975,453, which is a continuation of similarly titled U.S. patent application Ser. No. 11/074,513, filed Mar. 7, 2005, now U.S. Pat. No. 7,707,807, which claims the benefit of U.S. Provisional Patent Application Ser. No. 60/551,565, filed Mar. 8, 2004, entitled "Apparatus and Method For Molding and Assembling Containers With Stoppers and Filling Same;" U.S. patent application Ser. No. 12/715,821, filed Mar. 2, 2010, entitled "Method for Molding and Assembling Containers with Stopper and Filling Same," which is a continuation of similarly titled U.S. patent application Ser. No. 11/074,454, filed Mar. 7, 2005, now U.S. Pat. No. 7,669,390; U.S. patent application Ser. No. 11/339,966, filed Jan. 25, 2006, entitled "Container Closure With Overlying Needle Penetrable and Thermally Resealable Portion and Underlying Portion Compatible With Fat Containing Liquid Product, and Related Method," now U.S. Pat. No. 7,954,521, which, in turn, claims the benefit of U.S. Provisional patent application Ser. No. 60/647,049, filed Jan. 25, 2005, entitled "Container with Needle Penetrable and Thermally Resealable Stopper, Snap-Ring, and Cap for Securing Stopper;" U.S. patent application Ser. No. 12/861,354, filed Aug. 23, 2010, entitled "Ready To Drink Container With Nipple and Needle Penetrable and Laser Resealable Portion, and Related Method;" which is a divisional of similarly titled U.S. patent application Ser. No. 11/786,206, filed Apr. 10, 2007, now U.S. Pat. No. 7,780,023, which, into turn, claims the benefit of similarly titled U.S. Provisional Patent Application Ser. No. 60/790,684, filed Apr. 10, 2006; U.S. patent application Ser. No. 11/295,251, filed Dec. 5, 2005, entitled "One-Way Valve, Apparatus and Method of Using the Valve," now U.S. Pat. No. 7,322,491, which, in turn, claims the benefit of similarly titled U.S. Provisional Patent Application Ser. No. 60/644,130, filed Jan. 14, 2005, and similarly titled U.S. Provisional Patent Application Ser. No. 60/633,332, filed Dec. 4, 2004; U.S. patent application Ser. No. 12/789,565, filed May 28, 2010, entitled "Resealable Containers and Methods of Making, Filling and Resealing the Same," which is a continuation of U.S. patent application Ser. No. 11/933,272, filed Oct. 31, 2007, entitled "Resealable Containers and Assemblies for Filling and Resealing Same," now U.S. Pat. No. 7,726,357, which is a continuation of U.S. patent application Ser. No. 11/515,162, filed Sep. 1, 2006, entitled "Sealed Containers and Methods of Making and Filling Same," now U.S. Pat. No. 7,726,352; U.S. patent application Ser. No. 13/045,655, filed Mar. 11, 2011, entitled "Sterile Filling Machine Having Filling Station and E-Beam Chamber," which is a continuation of U.S. patent application Ser. No. 12/496,985, filed Jul. 2, 2009, entitled "Sterile Filling Machine Having Needle Filling Station and Conveyor," now U.S. Pat. No. 7,905,257, which is a continuation of U.S. patent application Ser. No. 11/527,775, filed Sep. 25, 2006, entitled "Sterile Filling Machine Having Needle Filling Station within E-Beam Chamber," now U.S. Pat. No. 7,556,066, which is a continuation of similarly titled U.S. patent application Ser. No. 11/103,803, filed Apr. 11, 2005, now U.S. Pat. No. 7,111,649, which is a continuation of similarly titled U.S. patent application Ser. No. 10/600,525, filed Jun. 19, 2003, now U.S. Pat. No. 6,929,040, which, in turn, claims the benefit of similarly-titled U.S. Provisional Patent Application Ser. No. 60/390,212, filed Jun. 19, 2002; U.S. patent application Ser. No. 13/326,177, filed Dec. 14, 2011, entitled "Device with Penetrable and Resealable Portion and Related Method," which is a continuation of similarly titled U.S. patent application Ser. No. 13/170,613, filed Jun. 28, 2011, which is a continuation of U.S. patent application Ser. No. 12/401,567, filed Mar. 10, 2009, entitled "Device with Needle Penetrable and Laser Resealable Portion and Related Method," now U.S. Pat. No. 7,967,034, which is a continuation of similarly titled U.S. patent application Ser. No. 11/933,300, filed Oct. 31, 2007, now U.S. Pat. No. 7,500,498; U.S. patent application Ser. No. 13/329,483, filed Apr. 30, 2011, entitled "Ready to Feed Container," which is a continuation of International Application Serial No. PCT/US2011/034703, filed Apr. 30, 2011, entitled "Ready to Feed Container and Method," which, in turn, claims the benefit of U.S. Provisional Patent Application Ser. No. 61/330,263 filed Apr. 30, 2010; and U.S. Provisional Patent Application Ser. No. 61/476,523, filed Apr. 18, 2011, entitled "Filling Needle and Method."

In other embodiments, the heat-sealable septum is sealed by contacting the septum with a heated probe, as disclosed, for example, in U.S. Pat. No. 6,604,561, issued Aug. 12, 2003, entitled "Medicament Vial Having a Heat-Sealable Cap, and Apparatus and Method for Filling the Vial," and/or a liquid sealing process as disclosed in co-pending U.S. patent application Ser. No. 13/745,721, filed Jan. 18, 2013, entitled "Device with Co-Molded Closure, One-Way Valve, Variable-Volume Storage Chamber and Anti-Spritz Feature and Related Method," which is hereby expressly incorporated by reference in its entirety as part of the present disclosure.

Once the container 301 is filled and resealed, the conveyor mechanism for the support 302 reverses direction (from left to right in FIG. 20), and conveys the filled and sealed container out of the processing space 310 in the position shown in FIGS. 20 and 21, so that a user can access the filled container 301 and remove it from the support 302. In alternative embodiments, the door 308 is opened and the sealed, filled container 301 is removed from the support 302 and apparatus 300 at the resealing station. Alternatively still, the apparatus has an opening on the end of the processing space 310 adjacent to the resealing station through which the container 301 is conveyed out of the processing space 310 or otherwise provides access to the filled container 301 for removal.

As noted above, apparatus 300 in different embodiments is manually or automatically operated. The control panel 315 includes a power switch, an ON/OFF operation switch, and is in operative communication with computerized systems that include software and/or programming to be used to control the amount and flow of substance, sealant, and/or sterilant used during the operation of apparatus 300, and also control the fluid flow of substance through and from the filling device 304. Further, the control panel 315 can be used to select from different types of substances, sealants, and/or sterilants, depending on the configuration of the substance supply and the needs of the user. As discussed above, the control panel 315 may control the movement of the support 302, and thus the container 301 to be filled, through the apparatus 300, which control may be automatic via one or more selectable programs installed in the apparatus, or via instruction of the operator as entered through the control panel 315.

Furthermore, as noted, control panel 315 is connected to other electrical components within apparatus 300, such as motors, processors, heaters, etc. To maintain the proper operating conditions for these electrical components, apparatus 300 includes an exhaust fan 313 on the top thereof that draws cooling air into and through the apparatus 300 and over the components, preventing overheating. Alternatively, the exhaust fan 313 is positioned on a side or back of the apparatus 300. Additionally, the electrical components of apparatus 300 are modularly installed therein, such that easy maintenance and exchange of separate electrical parts is possible as needed. For example, the electrical control for the sanitizing device 303 and the electrical control for the filling device 304 are located in separate modules or separate electrical panels, such that one can be replaced without affecting the other.

The apparatus 300 provides a process of filling and sealing a single container 301 at a time, in a continuous process, allowing for user-controlled, on-demand sequential filling of containers. Accordingly, after removal of the filled and sealed container 301, another (sealed) empty container 301 can be mounted on the support 302 and the above filling process repeated. During this operation, the filling device 304 is reused for subsequent fillings. This operation can be used for multiple container fillings, without changing the filling device 304.

However, if there is a need to change the filling device 304, for example due to a change in the substance to be dispensed therethrough or for any other reason, the filling device 304 can be removed and replaced. To do so, the cap 311 is replaced onto the needle 304. In this process, a user uses the control panel 315 to initiate this process. In effect, the reverse of the process to remove the cap 311 is performed.

As seen in FIG. 20, the cap 311 has been held in the cap grip 319 during the filling process. The support 302 is moved into the processing space 310 until aligned directly underneath the filling device 304. The filling device 304 is then moved downward until the cap 311 engages onto the filing device 304, e.g., snaps on, and the filling device is retracted to remove the cap up out of the cap grip 319.

In embodiments where the cap 311 is held in the storage position in the cap holder 312 throughout the filling and sealing process, cap 311 is removed from the cap holder 312 by moving the cap grip 319 into alignment underneath cap holder 312, the cap holder 312 is moved downward until the cap 311 engages and is retained by the cap grip 319, and the cap holder 312 is retracted upward, disengaging the cap 311 from the cap support 302. Next, the support 302 moves so that the cap 311 is positioned and aligned with the filling device 304. Filling device 304 is then lowered downward into the cap 311, engaging therewith, e.g., snapping on, and retracted upward with the cap secured thereto and clear of the cap grip 319. The support 302 is then moved to the position shown in FIG. 20 so that a user can remove and/or exchange the filling device 304.

The re-capping procedure is also performed when filling is complete, and before the apparatus 300 is shut down so that the filling device 304 is capped during periods of non-use. Advantageously, this process can be fully automated such that a user does not have to interact with an exposed portion of the filling device 304, such as the point of a needle, and thus sanitary and safe conditions can be maintained.

Figure 22:
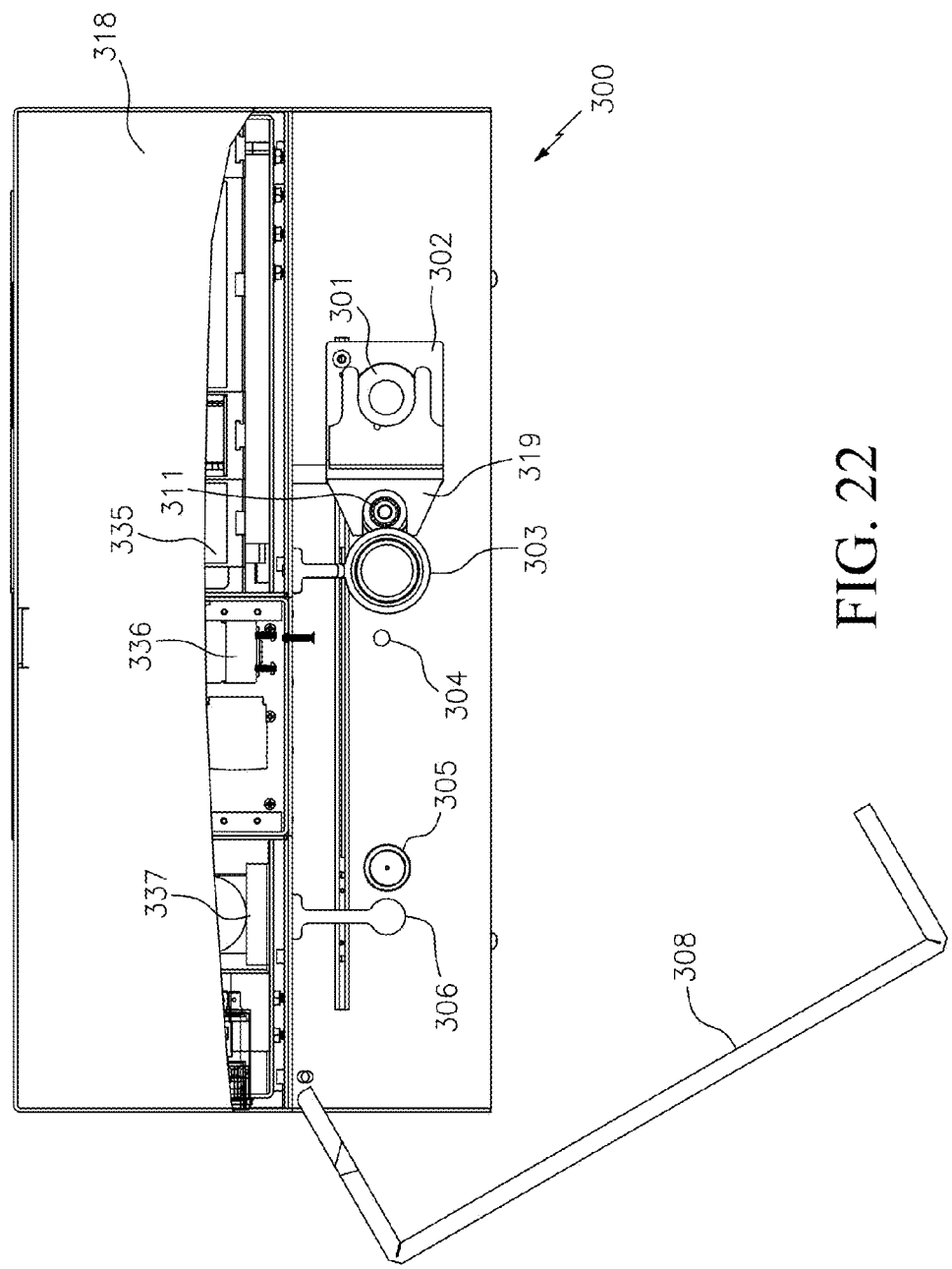
FIG. 22 is a top plan view of the apparatus of FIG. 20, with a partial cut-out showing internal components.
Figure 23:
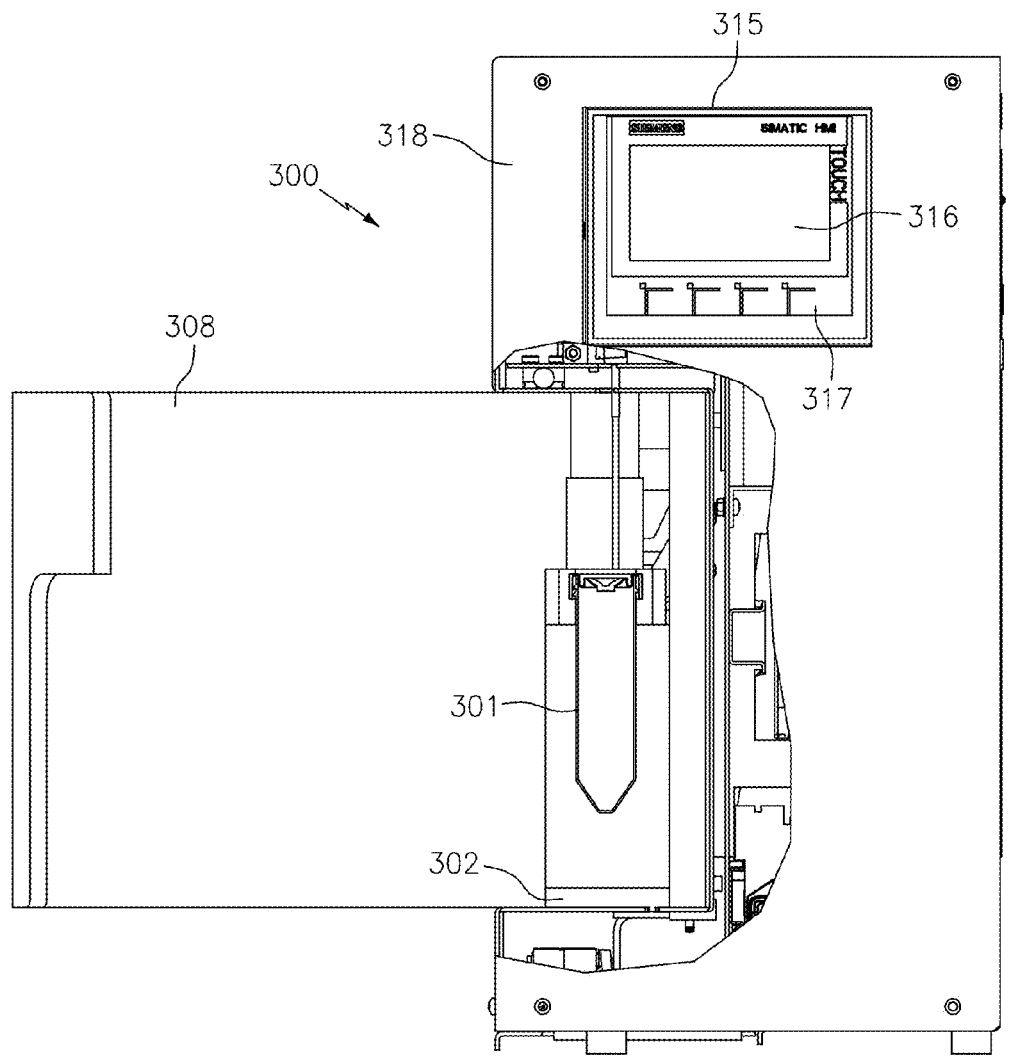
FIG. 23 is a right-side elevational view of the apparatus of FIG. 20, with a partial cut-out showing internal components.

Turning now to FIGS. 22-23, FIG. 22 partially illustrates the interior of the apparatus 300, including electrical and mechanical components 335 for the sanitizing station, electrical and mechanical components 336 for the filling station, and electrical and mechanical components 337 for the sealing station, each of which can be controlled by control panel 315.

FIG. 23 shows additional detail of the control panel 315, which includes a touchscreen display 316, and buttons 317 to control operation of apparatus 300. Control panel 315 in other embodiments includes analog controls, e.g., dials, switches, etc. In certain embodiments, the display 315 is a dynamic touch-screen that provides easy step-by-step operating instructions to guide an operator through the filling process, thereby reducing training time. Furthermore, the operating software for the apparatus 300 includes redundant safety measures to prevent and/or minimize malfunction and/or user error.

Apparatus 300, as described above, provides a filling process of a container with non-preserved (or, if desired, preserved) formulations in closed containers in a non-classified environment, and sealing thereof. Advantageously, this is as safe as accepted aseptic filling methods of preserved or unpreserved formulations in open containers in a controlled environment. Furthermore, the apparatus 300 is a compact apparatus that enables localized sterile filling on location. Because apparatus 300 provides sanitization within the apparatus 300, no clean room is necessary for filling containers 301.

Figure 24:
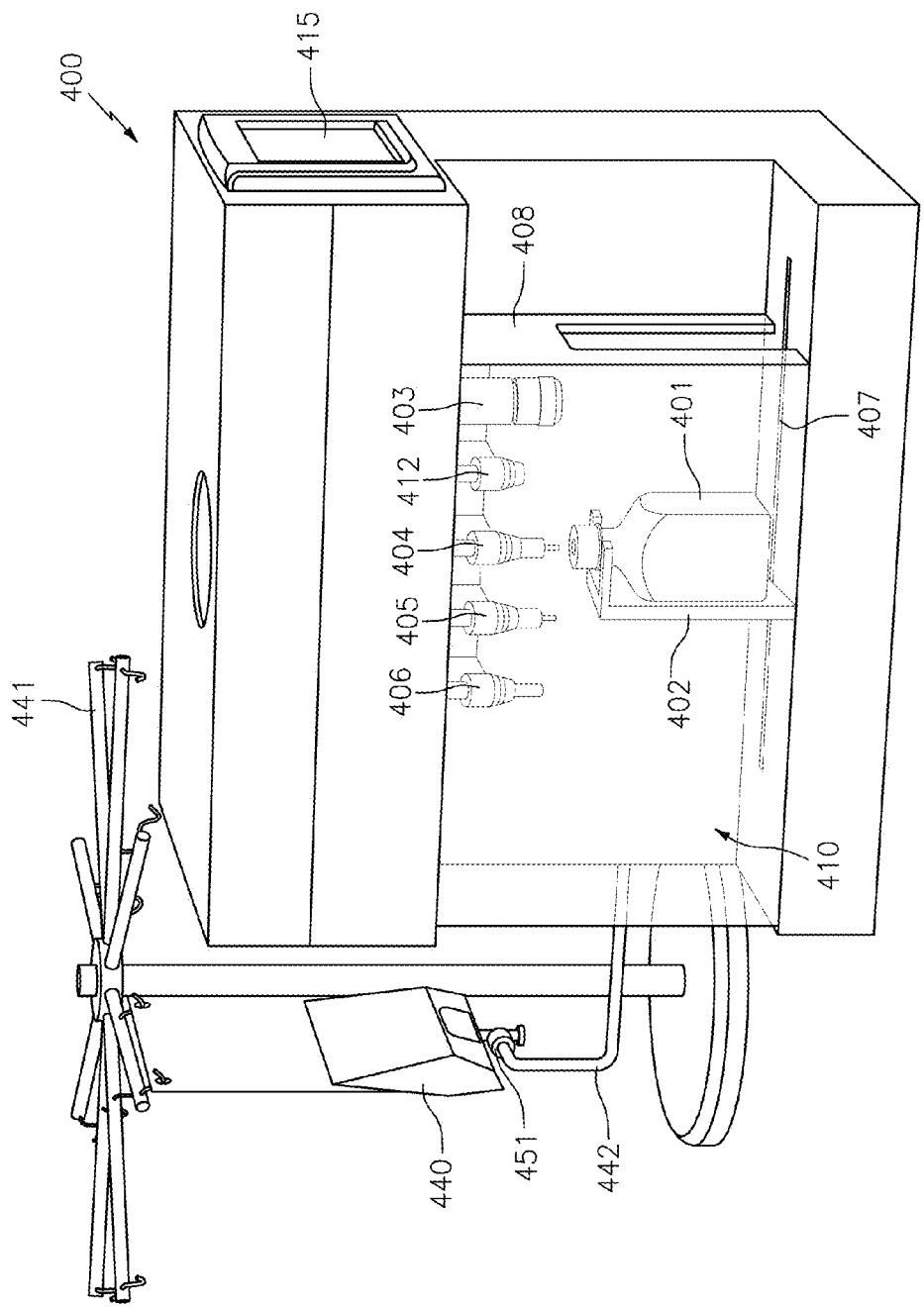
FIG. 24 is perspective view of another embodiment of an apparatus for filling and resealing sealed containers.

Turning now to FIG. 24, an alternative embodiment of a filling and sealing apparatus 400 is shown. Apparatus 400 is substantially similar to apparatus 300, and similar reference numbers are used for similar components and features, except preceded by the number "4" instead of the number "3." Accordingly, apparatus 400 is shown with a container 401 held by a support 402 that is conveyed through a processing space 410 including a door 408. Apparatus 400 includes a control panel 415, a sanitizing station including a sanitizing device 403, and a sealing station including a sealant dispenser 405 and a sealer device 406. As shown, apparatus 400, in contrast to apparatus 300, the cap holder 412 and the filling device 404 are switched in position, such that the cap holder 412 is adjacent to the sanitizing station, but the operation and method of filling and sealing of the container 401 is substantially the same as described above with respect to apparatus 300.

As shown in FIG. 24, the apparatus 400 is supplied with substance for filling into container 401 from one or more fluid sources and/or reservoirs that are separate from the apparatus 400. A substance supply 440, such as a disposable bag, pouch, or other type of container, is supported on a rack or carousel 441, which in some embodiments rotates and/or spins. The supply 440 is fluidly connected to apparatus 400, and thus filling device(s) 404, by a fluid line 442. The substance supply 440 is, in some embodiments, a sterile, hermetically sealed container that contains a sterile, non-preserved substance to be dispensed into container 401.

As noted, the substance supply 440 is fluidly connected to the apparatus 400 by the fluid line 442. The fluid line 442 contains a sterile connector 451, as discussed above, that permits the supply 440 to be connected to the apparatus 400 and formed from a sterile fluid path for the substance between the supply 440 and the apparatus 400. Thus, an entirely sterile fluid path sealed from the ambient atmosphere is maintained during the filling process from the substance supply 440, into the apparatus 400, through the filling device 404 and into the sealed chamber of the container. In other applications that do not utilize sterile substances or require sterile transfer or filling, the connectors need not be sterile connectors.

Carousel 441 is configured to hold multiple substance supplies 440, each connectable to the apparatus 400 via a sterile connector 451, such that a user can easily change which substance supply 440 is connected to apparatus 400. As such, a user of apparatus 400 can provide multiple supplies of the same substance, such that when one substance supply 440 empties, the empty supply can be quickly disconnected, and a replacement substance supply 400 may be quickly connected to the apparatus 400 to continue filling containers 401. Alternatively, different substances may be stored in difference substance supplies 440, such that a user can change the substance to be dispensed into container 401 with ease. During changing of the substance supply 440, the sterile fluid pathway, i.e., fluid line 442, is provided via the sterile connectors 451, which maintain the fluid pathways in a sealed condition with respect to the ambient atmosphere, even when the supply 440 is disconnected from the apparatus 400. Moreover, a change of substance supply 440 can be relatively quick, e.g., within a few minutes, by disconnecting the substance supply 440 from the fluid line 442 using a connector, and then attaching a second substance supply 440 to the fluid line 442. However, each substance supply may hold a sufficient volume of substance to fill multiple containers 401 without requiring changing the substance supply 440 often.

Furthermore, although shown with only one substance supply 440 connected to apparatus 400 with a single fluid line 442, apparatus 400 can be configurable to receive fluid from multiple substance supplies 440, and each substance supply 440 can be connected to apparatus 400 by a different sterile fluid line 442 and to a different filling device 404, for example apparatus 400 can include two or more filling devices 404. Accordingly, mixing of substances within a container 401 is permitted by the apparatus 400.

In this manner, it is possible to fill different substances into a single container 401, thereby creating a formulation from multiple substances in the container 401. Such processes are described, for example, in co-pending U.S. patent application Ser. No. 12/245,678, filed Oct. 3, 2008, entitled "Apparatus and Method for Formulating and Aseptically Filling Liquid Products," and U.S. patent application Ser. No. 12/245,681, filed Oct. 3, 2008, entitled "Apparatus and Method for Formulating and Aseptically Filling Liquid Products," which are hereby expressly incorporated by reference in their entireties as part of the present disclosure. It is also possible to fill different containers 401 with different substances easily. Accordingly, several different substances may be held on the carousel 441, and used as desired over the course of time to fill the particular substance desired on demand.

Alternatively, although shown as a rack or carousel 441, one or more fluid supplies may be housed in a separate storage container, device, or tank that can control and maintain appropriate temperatures, humidity levels, light levels, etc., such that any substances stored therein are not damaged while in a storage state. Such a storage container may be configured with one or more fluid lines that can fluidly communicate substance from the storage container to the apparatus 400 for filling containers 401. Furthermore, although shown with the substance supply 440 separate from the apparatus 400, the apparatus 400 can be configurable to house one or more substance supplies within the apparatus 400.

Figure 25:
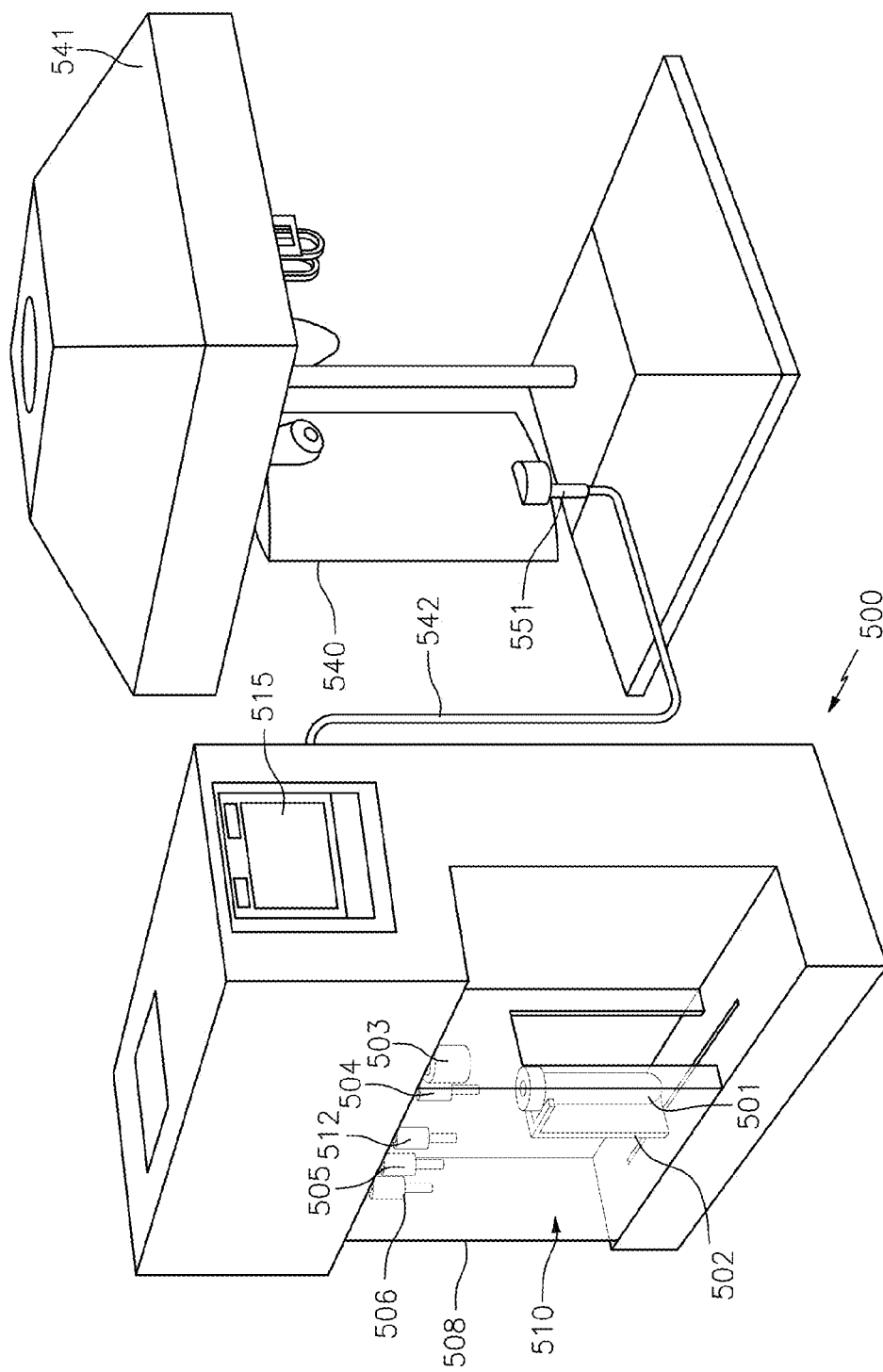
FIG. 25 is perspective view of another embodiment of an apparatus for filling and resealing sealed containers.

Turning now to FIG. 25, an alternative configuration of an apparatus 500 and carousel 541 is shown. The apparatus 500 and carousel 541, and other components shown therein, are substantially similar to the apparatus 400 and carousel 441 of FIG. 24, and like elements are similarly labeled, except preceded by the number "5" instead of "4." Apparatus 500 includes a control panel 515, and a processing space 510 including a sterilizing device 503, a filling device 504, a sealant dispenser 505, and a sealer device 506, housed within the processing space 510 including a door 508. The container 501 is held by support 502 which conveys the container 501 through the processing space 510 to fill and seal container 501, as described above. As shown, apparatus 500 is fluidly connected to a substance supply 540 by a fluid line 542 via a sterile connector 551, which is retained on a carousel 541. As shown, the carousel 541 is configured to support multiple substance supplies 540, and the substance supplies 540 may be fluidly connected to apparatus 500, and one or more filling devices 504, by one or more fluid lines 542, in a similar manner as described above with respect to apparatus 400.

Though the apparatuses 300, 400, 500 can be used to fill various containers or devices as describe above, other filling apparatuses may be employed, including that disclosed in co-pending U.S. patent application Ser. No. 13/861,502, filed Apr. 12, 2013, entitled "Modular Filling Apparatus and Method," which claims the benefit of similarly titled U.S. Provisional Patent Application No. 61/686,867, filed Apr. 13, 2012, each of which is hereby expressly incorporated by reference in its entirety as part of the present disclosure.

Advantageously, embodiments of the apparatuses disclosed herein can used in any setting where, e.g., small-scale sterile filling is desired, such as a laboratory setting with a desk-top apparatus. The apparatus is small and compact, and easily fits on a typical desk or bench top, and is easily moved and/or transported. Some embodiments of the apparatus are compact enough to fit within a carry-case or suitcase. Various embodiments are less than about 2 cubic feet (75 dm$^3$) in volume and weigh less than about 42 pounds (19 kg). Accordingly, the apparatus can be easily transferred from one location to another. In addition, the above-described apparatuses are user-friendly devices providing a turnkey sterile filling system. There is only a single electrical connection, and the apparatus is fully integrated to perform all the functions described above, without human interaction and/or human contamination. There is no need for vaporized hydrogen peroxide (VHP) or other fluid sterilant system, compressed air, filtered or sterile laminar flow environments, or any complex or costly isolators, though the apparatus in some embodiments could include a VHP supply for sanitation.

Figure 26:
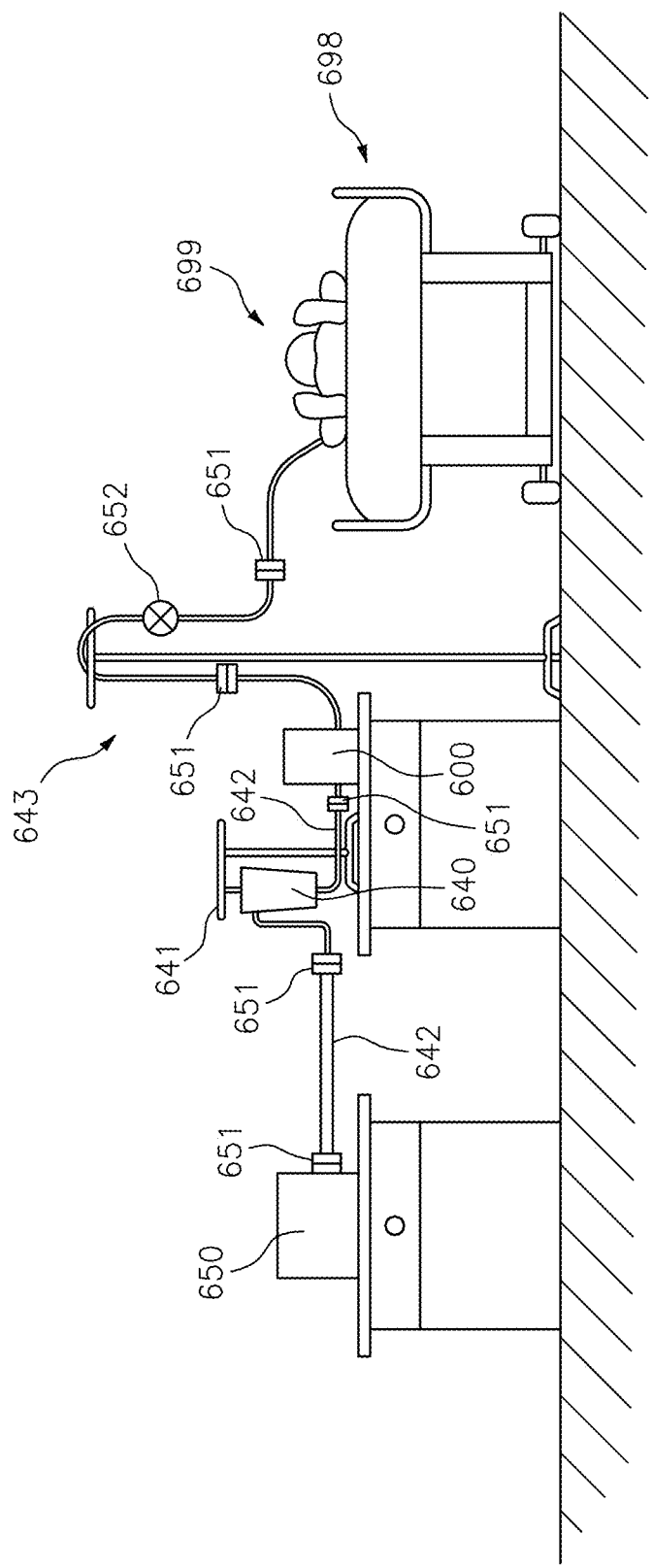
FIG. 26 is a schematic depiction of the apparatus of FIG. 25 providing substance to a patient.

Turning now to FIG. 26, a schematic depiction is shown of an apparatus, as described above, as used in a hospital setting, connecting an apparatus 600 providing a closed sterile fluid path 643 to a patient 699. As shown, patient 699 lies on a bed 698 in a patient care room. Apparatus 600, similar to apparatus 300, 400, and 500, described above, may be placed in a patient room on a table next to the patient 699, or may be placed in a different room and the filled, sealed container transported to the patient 699 room. A substance supply 640, held on a carousel 641, provides a supply of substance to apparatus 600 by a sterile fluid line 642. As shown, a tank 650 is also provided with a larger supply of substance, and is connected to the substance supply 640 by another sterile fluid line 642. Sterile connectors 651, such as those described above, may form part of the sterile fluid lines 642. In such manner, multiple substance containers can be connected to the apparatus 600, such that multiple substances can be selectively delivered to a patient, or different substances delivered to different patients.

To provide the patient with the substance from apparatus 600, the apparatus 600 is in sterile fluid communication with a patient through an IV or similar sterile fluid connector 643. In such embodiments, instead of the apparatus 600 delivering substance to a filling member to penetrate a container, the apparatus 600 delivers substance to the IV line. The sterile fluid line between the apparatus 600 and the patient 699 includes a sterile connector 651, as described above, so that the IV line can be disconnected from the apparatus while maintaining a sterile, sealed fluid path through the apparatus 600. Furthermore, an additional peristaltic pump 652 between the apparatus 600 and the patient 699 allows the fluid flow injection and supply to the patient can be precisely controlled by a patient care specialist.

The ability to disconnect the patient IV line from the apparatus and maintain a sterile fluid path, i.e., via sterile connector 651, along with the small and portable nature of the apparatus 600 as discussed above, allows the apparatus 600 to be moved from one patient treatment room to another to treat different patients. This advantageously avoids needing to move the patient to another location to administer the treatment, which might be medically detrimental to the patient. In addition, the above-described ability to quickly connect and disconnect one or more different substance supplies to the apparatus 600 permits a "standard" set of substances to be maintained with the apparatus for different treatments, and also, to replace substance supplies as needed with minimal downtime of the apparatus or disruption to patient treatments. Yet further, the apparatus 600 allows multiple dosing of a patient over time, where between such doses the IV line is disconnected from the apparatus via sterile connector 651, for patient comfort, mobility, or infusion of alternative substances, without compromising the sterile fluid pathway for subsequent doses.

In alternative embodiments, apparatus 600 is configured to fill containers, as described above, such as IV bags, which are then provided for patient use immediately and on-site in the patient's care room. As such, specific care defined IV bags may be filled in a patient care room, allowing for on-site, immediate response to needs of the patient.

Advantageously, a completely sterile delivery, from an original substance source to application to a patient is provided, wherein the substance is maintained sterile, and sealed with respect to ambient atmosphere, from the substance source, through sterile filling into a container or other device for patient delivery and, in turn, delivery from such container or device to a patient. For example, with reference to FIG. 26, in an alternative embodiment, substance source 640 is a sterile filled and enclosed substance source, such as a pouch, that includes a sterile connector for attachment to a sterile fluid line, for example the sterile connectors described and incorporated by reference above. The sterile connector of the substance source 640 is connected to a sterile fluid line 642 that is fluidly connected to the closed needle of the apparatus 600 (i.e., the sterile connector, flexible fluid line engageable by, for example, a peristaltic pump, and closed needle form a filling kit that is mounted in the filling apparatus 600 for a respective sterile fill). The apparatus 600 then fills a sterile container in accordance with the sterile filling and resealing process described above with a substance to be administered to a patient. The filled, sterile container also includes a sterile connector, for example the sterile connectors described and incorporated by reference above, and is removed from the apparatus 600. The filled, sterile container filled by apparatus 600 is then connected through its sterile connector to a sterile fluid line that is provided for delivery of the sterile filled substance to a patient, for example, a catheter or IV line. In such embodiment, the catheter or IV line includes a catheter or needle on its end opposite the sterile connector connected to the sterile container for delivery of the sterile filled substance to a patient. Accordingly, a completely closed, i.e., from the ambient atmosphere, and sterile process, from source to patient, is provided without risk of contamination of a sterile substance. Further, in some embodiments, a peristaltic pump is provided between the filled, sterile container and the patient to provide a controlled application of the substance to the patient. Moreover, advantageously, the substance source 640 and/or the apparatus 600 can easily and efficiently be changed when a different patient and/or different formulation of substance is to be used.

As may be recognized by those of ordinary skill in the pertinent art based on the teachings herein, numerous changes and modifications may be made to the above-described and other embodiments without departing from its scope as defined in the claims. For example, the components of the vial or other device and the filling device may take any of numerous different configurations, or may be made of any of numerous different materials, that are currently known, or that later become known. For example, rather than taking the form of a needle, the filling or injection member could take the form of a cannula. The device to be filled, on the other hand, could include a one-way filling valve, and an elastic septum that receives the filling cannula, forms an annular interface with the filling cannula, and decontaminates the filling cannula prior to opening the shutter or other enclosure on the cannula, engaging the one-way valve, and filling the sterile chamber of a device. The filling devices likewise may be employed in any of numerous different configurations, driven into and out of engagement with the devices to be filled in any of numerous different ways, and the filled devices may be transported on any of numerous different types of conveyors or in other ways. Similarly, the devices to be filled may take the form of any of numerous different containers or devices that are currently known, or that later become known, such as vials, pouches, tubes, syringes, single dose delivery devices and multiple dose delivery devices. Also, the filling device may be used to inject any of numerous different types of fluids or other substances into the vial or other device for any of numerous different applications, including, for example, medicaments, pharmaceuticals, vaccines, liquid nutrition products, supplements, and numerous other products that are currently known, or that later become known. In addition, the filling process may take place in any of numerous different types of ambient environments defining any of numerous different types of contamination or sterility assurance levels. Accordingly, this detailed description of embodiments is to be taken in an illustrative, as opposed to a limiting sense.

What is claimed is:
1. A method, comprising the following steps:
   (a) penetrating an elastic septum of a device with an injection member, wherein the device defines a sealed, empty, sterile chamber in fluid communication with the elastic septum;
   (b) during the penetrating step, forming an annular interface between the elastic septum and the injection member extending axially between a penetration point on an interior surface of the elastic septum in fluid communication with the sterile chamber and an exterior surface of the septum engaging the injection member, and de-contaminating the injection member by one or more of (i) friction between the elastic septum and injection member at the annular interface, or (ii) elongation of the elastic septum at the annular interface;

(c) introducing a substance through the injection member and into the sterile chamber of the device;

(d) withdrawing the injection member from the elastic septum;

(e) allowing the elastic septum to reseal itself at a penetration aperture resulting from withdrawal of the injection member; and (f) maintaining the chamber sterile throughout steps (a) through (e).

2. A method as defined in claim 1, further comprising performing the penetrating step in an ambient environment defining a level of contamination greater than about class 100 or ISO 5 and less than or equal to about class 100,000 or ISO 8.

3. A method as defined in claim 1, wherein the de-contaminating of the injection member includes achieving at least approximately a 3 log reduction in bio-burden at the annular interface between the elastic septum and injection member.

4. A method as defined in claim 3, wherein the de-contaminating of the injection member includes achieving at least approximately a 6 log reduction in bio-burden at the annular interface between the elastic septum and injection member.

5. A method as defined in claim 1, wherein the elastic septum includes a penetration zone defining an approximate dome-shape, and the penetration step includes penetrating the elastic septum in the dome-shaped penetration zone.

6. A method as defined in claim 5, wherein the elastic septum defines a substantially convex exterior surface, and a substantially concave interior surface opposite the convex exterior surface.

7. A method as defined in claim 6, wherein the interior surface of the septum defines a surface that is recessed relative to said interior surface extending substantially about the penetration zone.

8. A method as defined in claim 7, wherein the relatively recessed surface is a groove.

9. A method as defined in claim 8, further comprising, during the penetrating step, reducing the strain on the interior surface of the septum within the penetration zone with the groove.

10. A method as defined in claim 1, wherein the elastic septum defines a hardness within a range of about 20 to about 80 shore A.

11. A method as defined in claim 1, wherein the elastic septum defines a penetration zone that is penetrated by the injection member, and the penetration zone is shaped to enhance pressure exerted by the elastic septum onto the injection member during the penetrating step.

12. A method as defined in claim 1, wherein during the penetrating step, the interior surface of the elastic septum forms an initial crack at substantially maximum elongation of the elastic septum by the injection member.

13. A method as defined in claim 1, wherein the annular interface is defined by a portion of the penetrated elastic septum extending annularly about the injection member substantially throughout an axial distance extending between interior and exterior points of contact between the penetrated septum and injection member of at least about ½ mm.

14. A method as defined in claim 1, wherein, during the penetrating step, the annular interface between the elastic septum and injection member defines a substantially inverted, frusto-conical shape.

15. A method as defined in claim 1, wherein a coefficient of friction of the septum-engaging surface of the injection member is less than a coefficient of friction of the penetrated portion of the elastic septum.

16. A method as defined in claim 1, wherein the injection member includes at least one port for dispensing the substance from the injection member, and the method further includes sealing the port with respect to ambient atmosphere until at least a portion of the port is in fluid communication with the sterile chamber, and moving one or more of a closure or the port of the injection member from a closed position sealing the port with respect to ambient atmosphere to an open position opening the port into fluid communication with the sterile chamber, and further comprising introducing a toxic substance through the injection member and into the sterile chamber of the device, and using the closure to prevent any exposure of the toxic substance to the ambient atmosphere throughout steps a) through e).

17. A method as defined in claim 1, wherein the de-contaminating of the injection member includes exerting pressure with the elastic septum onto the injection member at the annular interface between the elastic septum and injection member and, in turn, killing organisms at the interface.

18. A method as defined in claim 1, wherein the elastic septum defines a penetration zone that is penetrated by the injection member, and the penetration zone of the elastic septum defines a thickness prior to penetration within a range of about ½ to about two times an outer diameter of the injection member.

19. A method as defined in claim 1, wherein the elastic septum defines a penetration zone including a recess defining a reduced thickness of the elastic septum, and the penetrating step includes penetrating the elastic septum at the reduced thickness of the penetration zone.

20. A method as defined in claim 19, wherein the penetration zone recess defines a substantially frusto-conical shape.

21. A method as defined in claim 19, wherein the injection member includes a penetrating tip defining a first included angle, and the penetration zone recess defines a second included angle that is substantially the same as the first included angle.

22. A device that is sterile fillable by an injection member defining a port that is normally sealed with respect to ambient atmosphere and can be opened to dispense substance from the injection member therethrough, wherein the device comprises:

a body defining a sealed, empty, sterile chamber; and an elastic septum in fluid communication with the sealed, empty, sterile chamber, wherein (A) the elastic septum is penetrable by the injection member and forms an annular interface between the elastic septum and the injection member extending axially between (i) a penetration point on an interior surface of the elastic septum in fluid communication with the sterile chamber, and (ii) an exterior surface of the septum engaging the injection member, and (B) relative movement of the injection member and elastic septum de-contaminates the injection member through one or more of (i) friction between the elastic septum and injection member at the annular interface, or (ii) elongation of the elastic septum at the annular interface.

23. A device as defined in claim 22, wherein relative movement of the injection member and elastic septum opens the port of the injection member after decontaminating the injection member at the annular interface and at least part of the port is passed through the septum, and opens the port of the injection member into fluid communication with the sterile chamber to dispense substance from the injection member into the sterile chamber.

24. A device as defined in claim 22, wherein the relative movement of the injection member and elastic septum de-contaminates the injection member by at least approximately a 3 log reduction in bio-burden at the annular interface between the elastic septum and injection member.

25. A device as defined in claim 24, wherein the relative movement of the injection member and elastic septum de-contaminates the injection member by at least approximately a 6 log reduction in bio-burden at the annular interface between the elastic septum and injection member.

26. A device as defined in claim 22, wherein the elastic septum includes a penetration zone penetrable by the injection member and defining an approximate dome-shape.

27. A device as defined in claim 26, wherein the elastic septum defines a substantially convex exterior surface, and a substantially concave interior surface opposite the convex exterior surface.

28. A device as defined in claim 27, wherein the interior surface of the septum defines a surface that is recessed relative to said interior surface extending substantially about the penetration zone.

29. A device as defined in claim 28, wherein the relatively recessed surface is a groove.

30. A device as defined in claim 22, further including means for reducing the strain on the interior surface of the septum during penetration thereof by the injection member.

31. A device as defined in claim 22, wherein the elastic septum defines a hardness within a range of about 20 to about 80 shore A.

32. A device as defined in claim 22, wherein the elastic septum defines a penetration zone that is penetrable by the injection member, and the penetration zone is shaped to enhance pressure exerted by the elastic septum onto the injection member during penetration thereof by the injection member.

33. A device as defined in claim 22, wherein the annular interface is defined by a portion of the penetrated elastic septum extending annularly about the injection member substantially throughout an axial distance extending between interior and exterior points of contact between the penetrated septum and injection member of at least about ½ mm.

34. A device as defined in claim 22, wherein the annular interface between the elastic septum and injection member defines a substantially inverted, frusto-conical shape.

35. A device as defined in claim 22, wherein a coefficient of friction of the penetrated portion of the elastic septum is greater than a coefficient of friction of the septum-engaging surface of the injection member.

36. A device as defined in claim 22, wherein the elastic septum is configured to exert pressure onto the injection member at the annular interface between the elastic septum and injection member to thereby kill organisms at the interface.

37. A device as defined in claim 22, wherein the elastic septum defines a penetration zone that is penetrated by the injection member, and the penetration zone of the elastic septum defines a thickness prior to penetration within a range of about ½ to about two times an outer diameter of the injection member.

38. A device as defined in claim 22, wherein the elastic septum defines a penetration zone including a recess defining a reduced thickness of the elastic septum that is penetrated by the injection member.

39. A device as defined in claim 38, wherein the penetration zone recess defines a substantially frusto-conical shape.

40. A device as defined in claim 38, wherein the injection member includes a penetrating tip defining a first included angle, and the penetration zone recess defines a second included angle that is substantially the same as or greater than the first included angle.

41. A device as defined in claim 22 in combination with a filling device including an injection member defining a port that is normally sealed with respect to ambient atmosphere and can be opened to dispense substance from the injection member therethrough.

42. A device that is sterile filled by an injection member including means for sealing an interior of the injection member with respect to ambient atmosphere and for opening to dispense substance from the injection member therethrough, wherein the device comprises:
    first means defining a sealed, empty, sterile chamber; and
    second means in fluid communication with the sealed, empty, sterile chamber that is penetrable by the injection member (A) for forming an annular interface between the second means and the injection member extending axially between (i) a penetration point on an interior surface of the second means in fluid communication with the sterile chamber, and (ii) an exterior surface of the second means engaging the injection member, and (B) for de-contaminating the injection member through one or more of (i) friction between the second means and injection member at the annular interface, or (ii) elongation of the second means at the annular interface.

* * * * *